(12) United States Patent
Rappaport et al.

(10) Patent No.: US 9,575,045 B2
(45) Date of Patent: Feb. 21, 2017

(54) SIGNAL PROCESSING METHODS AND SYSTEMS FOR EXPLOSIVE DETECTION AND IDENTIFICATION USING ELECTROMAGNETIC RADIATION

(71) Applicant: Northeastern University, Boston, MA (US)

(72) Inventors: Carey Rappaport, Wellesley, MA (US); Jose Angel Martinez-Lorenzo, Boston, MA (US)

(73) Assignee: Northeastern University, Boston, MA (US)

( * ) Notice: Subject to any disclaimer, the term of this patent is extended or adjusted under 35 U.S.C. 154(b) by 454 days.

(21) Appl. No.: 13/968,746

(22) Filed: Aug. 16, 2013

(65) Prior Publication Data

US 2014/0070111 A1 Mar. 13, 2014

Related U.S. Application Data

(60) Provisional application No. 61/684,287, filed on Aug. 17, 2012.

(51) Int. Cl.
*G01S 13/89* (2006.01)
*G01N 33/22* (2006.01)
*G01N 23/083* (2006.01)

(52) U.S. Cl.
CPC ......... *G01N 33/227* (2013.01); *G01N 23/083* (2013.01)

(58) Field of Classification Search
CPC ............................ G01N 23/083; G01N 33/227

USPC .......................................................... 342/22
See application file for complete search history.

(56) References Cited

U.S. PATENT DOCUMENTS

| | | | | |
|---|---|---|---|---|
| 6,480,141 B1* | 11/2002 | Toth | ....................... | G01N 22/00 324/639 |
| 6,950,054 B1* | 9/2005 | Steinway | ................ | G01S 7/412 342/173 |
| 6,967,612 B1* | 11/2005 | Gorman | .................. | G01S 7/412 342/175 |
| 8,723,717 B2* | 5/2014 | Saito | ........................ | G01S 7/41 342/176 |
| 2004/0140924 A1* | 7/2004 | Keller | ................ | G01N 21/3581 342/22 |
| 2004/0183712 A1* | 9/2004 | Levitan | .................. | F41H 13/00 342/22 |
| 2005/0099330 A1* | 5/2005 | Hausner | .................. | G01S 7/025 342/22 |

(Continued)

*Primary Examiner* — Marcus Windrich
(74) *Attorney, Agent, or Firm* — Hamilton, Brook, Smith & Reynolds, P.C.

(57) ABSTRACT

In some aspects, the disclosure is directed to signal processing methods and systems for identifying a material on a body of a person using electromagnetic radiation. A radar system may measure a first reflection of radiation incident on a body of a person. The first reflection may be from a surface of the body. The radar system may measure a second reflection of the radiation. The second reflection may be from a first material residing on or proximate to the surface of the body. An analyzer may determine, relative to the first reflection, a delay in the second reflection due to propagation of a portion of the radiation through the first material. The analyzer may determine, based on the delay, at least one of: the first material and a dielectric constant of the first material.

20 Claims, 16 Drawing Sheets

(56) References Cited

U.S. PATENT DOCUMENTS

| | | | |
|---|---|---|---|
| 2007/0030195 A1* | 2/2007 | Steinway | G01S 7/412 342/22 |
| 2007/0052576 A1* | 3/2007 | Hausner | G01S 7/024 342/22 |
| 2007/0194976 A1* | 8/2007 | Reed | G01S 7/024 342/22 |
| 2008/0169961 A1* | 7/2008 | Steinway | A61B 5/05 342/27 |
| 2011/0084868 A1* | 4/2011 | Daly | G01S 7/03 342/22 |
| 2012/0194376 A1* | 8/2012 | Daly | G01S 13/887 342/22 |
| 2012/0235849 A1* | 9/2012 | Tatoian | G01S 13/0209 342/21 |
| 2013/0076556 A1* | 3/2013 | Boulais | G01S 13/887 342/22 |

* cited by examiner

SIGNAL PROCESSING METHODS AND SYSTEMS FOR EXPLOSIVE DETECTION AND IDENTIFICATION USING ELECTROMAGNETIC RADIATION

RELATED APPLICATION

This application claims priority to U.S. Provisional Patent Application No. 61/684,287, entitled "SIGNAL PROCESSING ALGORITHM FOR EXPLOSIVE DETECTION AND IDENTIFICATION USING ELECTROMAGNETIC RADIATION", filed Aug. 17, 2012, which is incorporated herein by reference in its entirety for all purposes.

FIELD OF THE DISCLOSURE

This disclosure generally relates to systems and methods for detection of concealed or unknown objects and materials. In particular, this disclosure relates to systems and methods for detection and identification of explosive and other materials using electromagnetic radiation.

BACKGROUND OF THE DISCLOSURE

In conventional systems for surveillance and detection purposes, images based on X-ray, conventional cameras, infra-red cameras and other techniques may be employed. These techniques focus on generating an image that profiles a detectable shape, outline and/or movement of an object. These characteristics may be reviewed by a person or processed using machine recognition. However, although characteristics like shapes and outlines may help to detect the presence or suspected presence of an object, manual intervention and follow-up is typically needed to verify the detection, and to test an unknown material for identification or threat potential. The latter may require a different process or means to augment the initial imaging step, such as the use of sniffer dogs or a physical analysis of a sample of the material to identify the material. Such means may be considered intrusive and/or offensive to the subject, and may add significant delay to the overall process of identifying an unknown substance or object.

BRIEF SUMMARY OF THE DISCLOSURE

Described herein are systems and methods for identifying a material on a body of a person using electromagnetic radiation. The present systems and methods can be used to detect and/or identify one or more materials (e.g., explosive materials) and objects that a subject may carry, wear or conceal. An electromagnetic system may be used to measure an electromagnetic response from the subject. For example, the system may detect an electromagnetic excitation from a subject wearing an explosive material or object under clothing. The system may process reflections or scattered field from the subject to detect and identify a material on or close to the subject's body. The system may include an electromagnetic-based imager to collect the scattered field from an object of interest. The system may include an analyzer to distinguish between different materials based on the image. The analyzer may distinguish between metallic and dielectric materials based on signatures in the image. For the case in which a dielectric material is detected, the analyzer may determine a dielectric constant of the material based on a delayed reflection due to propagation of radiation through the material. As such, an unknown or explosive compound such as TNT or RDX, concealed under clothing by a potential suicide bombers for example, may be detected and identified using the same electromagnetic-based system.

In some aspects, the present disclosure pertains to a method of identifying a material on a body of a person using electromagnetic radiation. The method may include measuring, by a radar system, a first reflection of radiation incident on a body of a person. The first reflection may be from a surface of the body. The radar system may measure a second reflection of the radiation. The second reflection may be from a first material residing on or proximate to the surface of the body. An analyzer may determine, relative to the first reflection, a delay in the second reflection due to propagation of a portion of the radiation through the first material. The analyzer may determine, based on the delay, at least one of: the first material and a dielectric constant of the first material.

In some embodiments, the analyzer determines that the first material comprises a dielectric material based on detection of the delay. The analyzer or the radar system may determine a thickness of the first material from a time delay between a third reflection of the radiation and the first reflection, the third reflection from a surface of the first material. The analyzer may determine the dielectric constant based at least in part on the thickness of the first material. The analyzer may determine that the first material comprises a first type of explosive material based on the dielectric constant. The analyzer may determine the dielectric constant of the first material from a predefined map between delay characteristics and corresponding dielectric constant values. The analyzer may identify the first material from a predefined map between delay characteristics and corresponding materials.

In certain embodiments, the radar system may generate an electromagnetic-based image identifying the first reflection and the second reflection. The radar system or analyzer may determine that a second material residing on or proximate to the surface of the body comprises a metallic material, based on an abrupt variation in pixel intensity in the image. The radar system or analyzer may determine, from the image, at least one of: the delay and a thickness of the first material.

In some aspects, the present disclosure pertains to a system of identifying a material on a body of a person using electromagnetic radiation. The system may include an electromagnetic-based imager providing a measurement of a first reflection of radiation incident on a body of a person. The first reflection may be from a surface of the body. The electromagnetic-based imager may provide a measurement of a second reflection of the radiation. The second reflection may be from a first material residing on or proximate to the surface of the body. An analyzer may determine, relative to the first reflection, a delay in the second reflection due to propagation of a portion of the radiation through the first material. The analyzer may determine, based on the delay, at least one of: the first material and a dielectric constant of the first material.

In some embodiments, the analyzer determines that the first material comprises a dielectric material based on detection of the delay. The analyzer may determine a thickness of the first material from a time delay between a third reflection of the radiation and the first reflection, the third reflection from a surface of the first material. The analyzer may determine the dielectric constant based at least in part on the thickness of the first material. The analyzer may determine that the first material comprises a first type of explosive material based on the dielectric constant. The analyzer may determine the dielectric constant of the first material from a predefined map between delay characteristics and corresponding dielectric constant values. The analyzer may identify the first material from a predefined map between delay characteristics and corresponding materials.

In some embodiments, the electromagnetic-based imager generates an image identifying the first reflection and the second reflection. The analyzer may determine that a second material residing on or proximate to the surface of the body comprises a metallic material, based on an abrupt variation in pixel intensity in the image. The analyzer may determine, from the image, at least one of: the delay and a thickness of the first material.

The details of various embodiments of the invention are set forth in the accompanying drawings and the description below.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

Figure 1A:
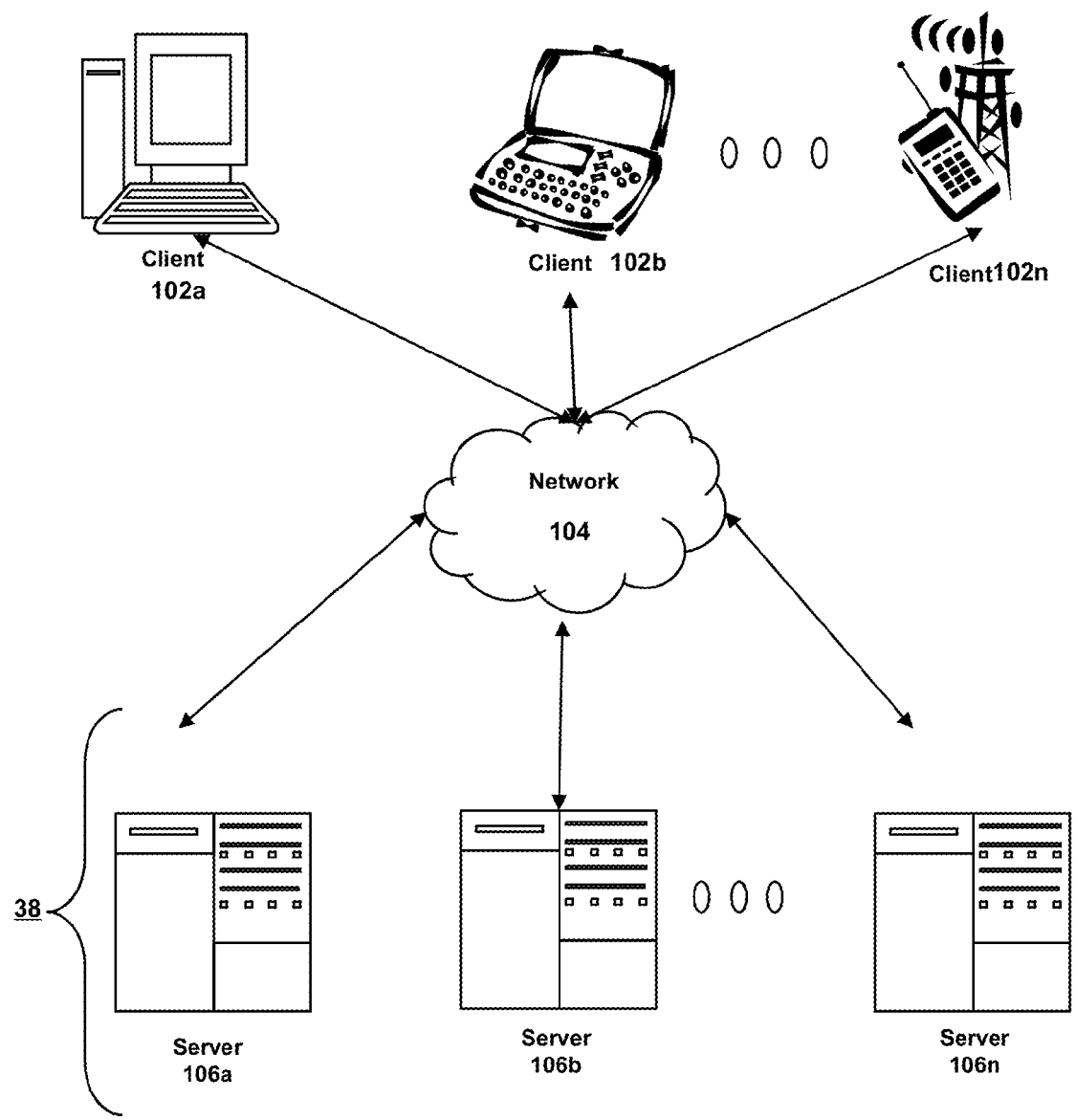
FIG. 1A is a block diagram depicting an embodiment of a network environment comprising client machines in communication with remote machines.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

For purposes of reading the description of the various embodiments below, the following descriptions of the sections of the specification and their respective contents may be helpful:

Section A describes a network environment and computing environment which may be useful for practicing embodiments described herein; and Section B describes embodiments of systems and methods for identifying a material on a body of a person using electromagnetic radiation.

A. Computing and Network Environment

Prior to discussing specific embodiments of the present solution, it may be helpful to describe aspects of the operating environment as well as associated system components (e.g., hardware elements) in connection with the methods and systems described herein. Referring to FIG. 1A, an embodiment of a network environment is depicted. In brief overview, the network environment includes one or more clients 101a-101n (also generally referred to as local machine(s) 101, client(s) 101, client node(s) 101, client machine(s) 101, client computer(s) 101, client device(s) 101, endpoint(s) 101, or endpoint node(s) 101) in communication with one or more servers 106a-106n (also generally referred to as server(s) 106, node 106, or remote machine(s) 106) via one or more networks 104. In some embodiments, a client 101 has the capacity to function as both a client node seeking access to resources provided by a server and as a server providing access to hosted resources for other clients 101a-101n.

Although FIG. 1A shows a network 104 between the clients 101 and the servers 106, the clients 101 and the servers 106 may be on the same network 104. The network 104 can be a local-area network (LAN), such as a company Intranet, a metropolitan area network (MAN), or a wide area network (WAN), such as the Internet or the World Wide Web. In some embodiments, there are multiple networks 104 between the clients 101 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be any type and/or form of network and may include any of the following: a point-to-point network, a broadcast network, a wide area network, a local area network, a telecommunications network, a data communication network, a computer network, an ATM (Asynchronous Transfer Mode) network, a SONET (Synchronous Optical Network) network, a SDH (Synchronous Digital Hierarchy) network, a wireless network and a wireline network. In some embodiments, the network 104 may comprise a wireless link, such as an infrared channel or satellite band. The topology of the network 104 may be a bus, star, or ring network topology. The network 104 may be of any such network topology as known to those ordinarily skilled in the art capable of supporting the operations described herein. The network may comprise mobile telephone networks utilizing any protocol(s) or standard(s) used to communicate among mobile devices, including AMPS, TDMA, CDMA, GSM, GPRS, UMTS, WiMAX, 3G or 4G. In some embodiments, different types of data may be transmitted via different protocols. In other embodiments, the same types of data may be transmitted via different protocols.

In some embodiments, the system may include multiple, logically-grouped servers 106. In one of these embodiments, the logical group of servers may be referred to as a server farm 38 or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous—one or more of the servers 106 or machines 106 can operate according to one type of operating system platform (e.g., WINDOWS, manufactured by Microsoft Corp. of Redmond, Wash.), while one or more of the other servers 106 can operate on according to another type of operating system platform (e.g., Unix or Linux).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualize physical hardware, and execute virtual machines that provide access to computing environments. Hypervisors may include those manufactured by VMWare, Inc., of Palo Alto, Calif.; the Xen hypervisor, an open source product whose development is overseen by Citrix Systems, Inc.; the VirtualServer or virtual PC hypervisors provided by Microsoft or others.

In order to manage a machine farm 38, at least one aspect of the performance of servers 106 in the machine farm 38 should be monitored. Typically, the load placed on each server 106 or the status of sessions running on each server 106 is monitored. In some embodiments, a centralized service may provide management for machine farm 38. The centralized service may gather and store information about a plurality of servers 106, respond to requests for access to resources hosted by servers 106, and enable the establishment of connections between client machines 101 and servers 106.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store.

Server 106 may be a file server, application server, web server, proxy server, appliance, network appliance, gateway, gateway, gateway server, virtualization server, deployment server, SSL VPN server, or firewall. In one embodiment, the server 106 may be referred to as a remote machine or a node. In another embodiment, a plurality of nodes 290 may be in the path between any two communicating servers.

In one embodiment, the server 106 provides the functionality of a web server. In another embodiment, the server 106a receives requests from the client 101, forwards the requests to a second server 206b and responds to the request by the client 101 with a response to the request from the server 106b. In still another embodiment, the server 106 acquires an enumeration of applications available to the client 101 and address information associated with a server 106' hosting an application identified by the enumeration of applications. In yet another embodiment, the server 106 presents the response to the request to the client 101 using a web interface. In one embodiment, the client 101 communicates directly with the server 106 to access the identified application. In another embodiment, the client 101 receives output data, such as display data, generated by an execution of the identified application on the server 106.

Figure 1B:
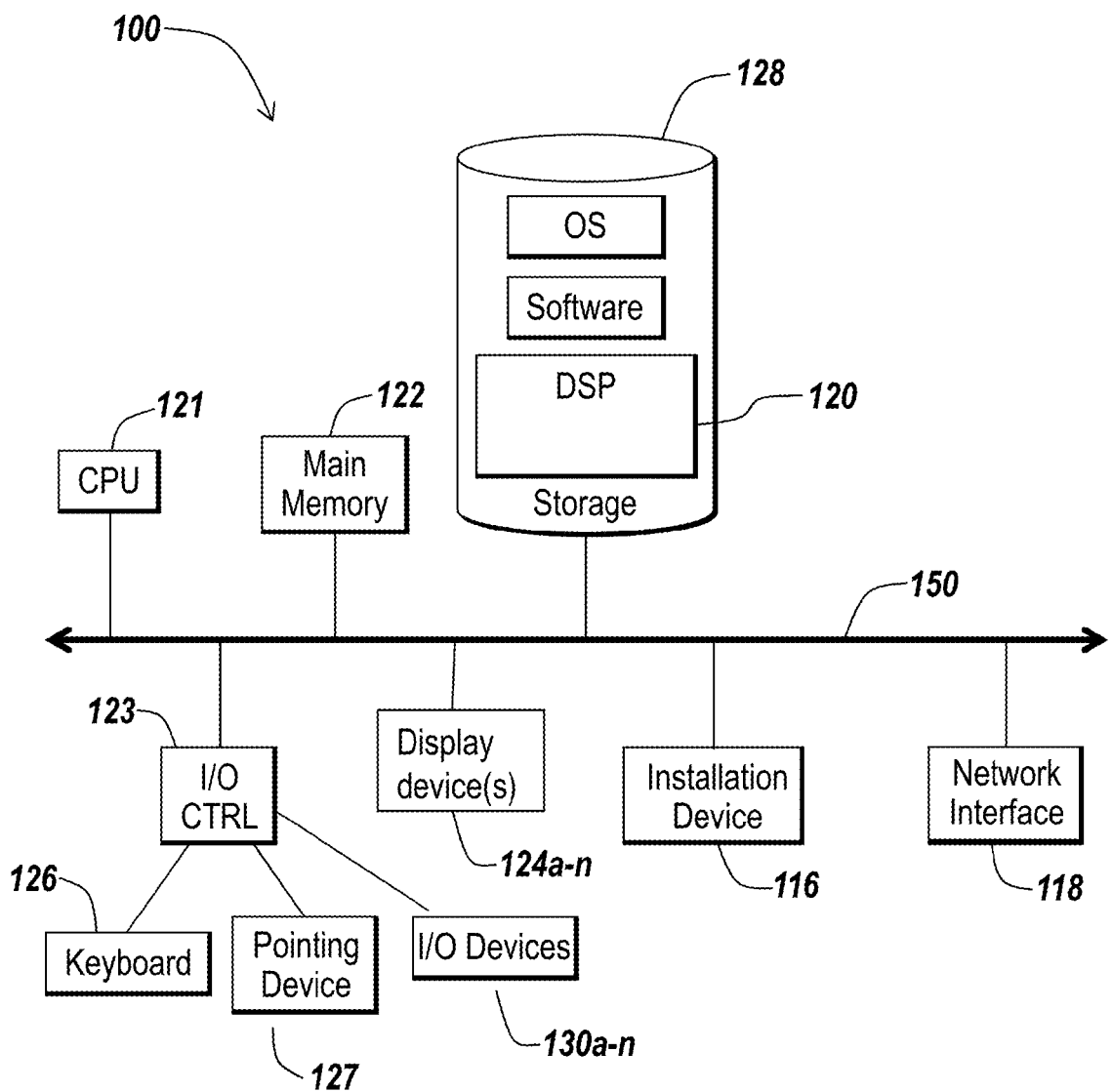
FIGS. 1B and 1C are block diagrams depicting embodiments of computing devices useful in connection with the methods and systems described herein.
Figure 1C:
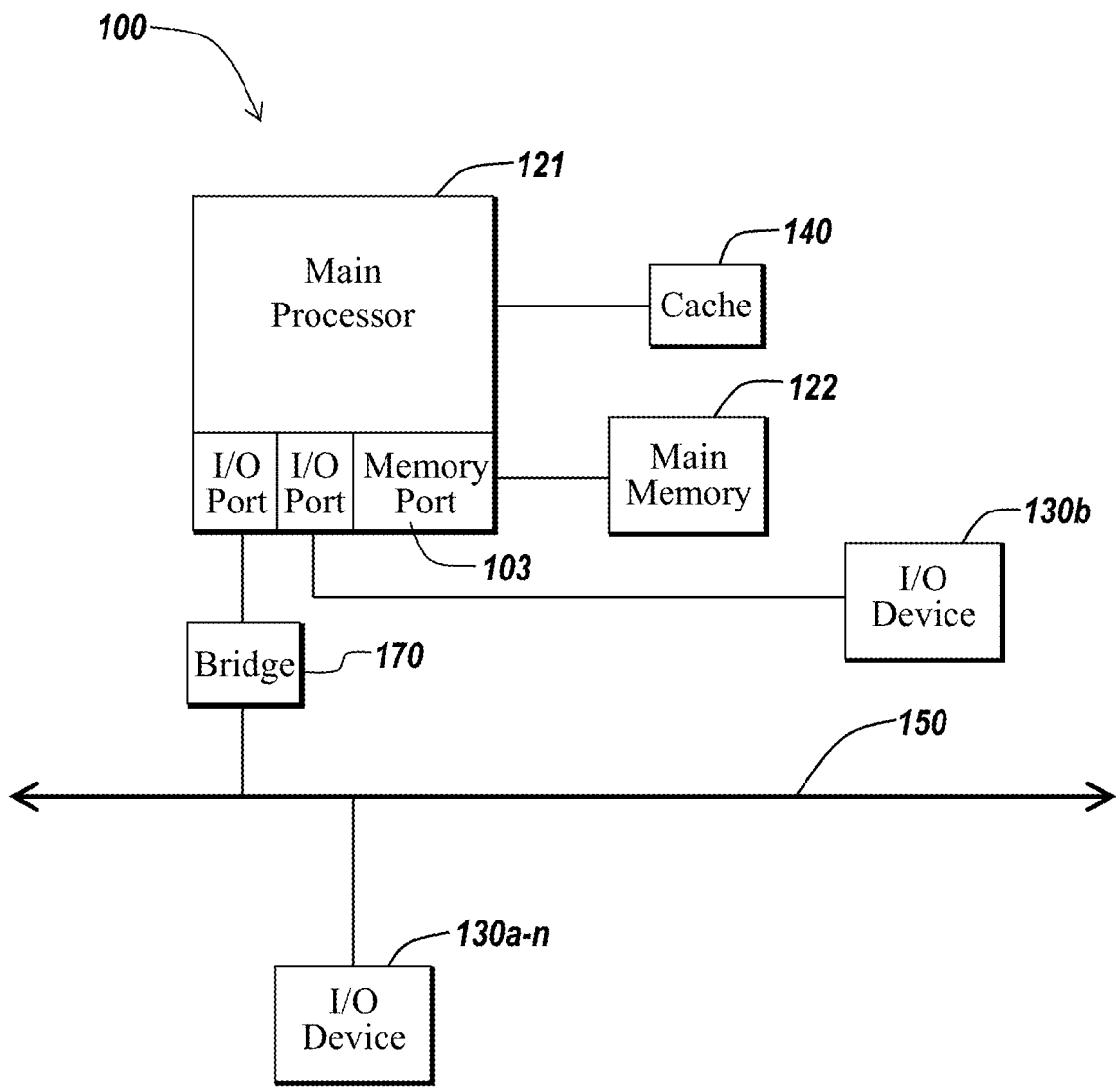

The client 101 and server 106 may be deployed as and/or executed on any type and form of computing device, such as a computer, network device or appliance capable of communicating on any type and form of network and performing the operations described herein. FIGS. 1B and 1C depict block diagrams of a computing device 100 useful for practicing an embodiment of the client 101 or a server 106. As shown in FIGS. 1B and 1C, each computing device 100 includes a central processing unit 121, and a main memory unit 122. As shown in FIG. 1B, a computing device 100 may include a storage device 128, an installation device 116, a network interface 118, an I/O controller 123, display devices 124a-101n, a keyboard 126 and a pointing device 127, such as a mouse. The storage device 128 may include, without limitation, an operating system and/or software. As shown in FIG. 1C, each computing device 100 may also include additional optional elements, such as a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, such as: those manufactured by Intel Corporation of Mountain View, Calif.; those manufactured by Motorola Corporation of Schaumburg, Ill.; those manufactured by International Business Machines of White Plains, N.Y.; or those manufactured by Advanced Micro Devices of Sunnyvale, Calif. The computing device 100 may be based on any of these processors, or any other processor capable of operating as described herein.

Main memory unit 122 may be one or more memory chips capable of storing data and allowing any storage location to be directly accessed by the microprocessor 121, such as Static random access memory (SRAM), Burst SRAM or SynchBurst SRAM (BSRAM), Dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDEC SRAM, PC 100 SDRAM, Double Data Rate SDRAM (DDR SDRAM), Enhanced SDRAM (ESDRAM), SyncLink DRAM (SLDRAM), Direct Rambus DRAM (DRDRAM), Ferroelectric RAM (FRAM), NAND Flash, NOR Flash and Solid State Drives (SSD). The main memory 122 may be based on any of the above described memory chips, or any other available memory chips capable of operating as described herein. In the embodiment shown in FIG. 1B, the processor 121 communicates with main memory 122 via a system bus 150 (described in more detail below). FIG. 1C depicts an embodiment of a computing device 100 in which the processor communicates directly with main memory 122 via a memory port 103. For example, in FIG. 1C the main memory 122 may be DRDRAM.

FIG. 1C depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1C, the processor 121 communicates with various I/O devices 130 via a local system bus 150. Various busses may be used to connect the central processing unit 121 to any of the I/O devices 130, including a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display 124, the processor 121 may use an Advanced Graphics Port (AGP) to communicate with the display 124. FIG. 1C depicts an embodiment of a computer 100 in which the main processor 121 may communicate directly with I/O device 130b, for example via HYPERTRANSPORT, RAPIDIO, or INFINIBAND communications technology. FIG. 1C also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices include keyboards, mice, trackpads, trackballs, microphones, dials, touch pads, and drawing tablets. Output devices include video displays, speakers, inkjet printers, laser printers, projectors and dye-sublimation printers. The I/O devices may be controlled by an I/O controller 123 as shown in FIG. 1B. The I/O controller may control one or more I/O devices such as a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices such as the USB Flash Drive line of devices manufactured by Twintech Industry, Inc. of Los Alamitos, Calif.

Referring again to FIG. 1B, the computing device 100 may support any suitable installation device 116, such as a disk drive, a CD-ROM drive, a CD-R/RW drive, a DVD-ROM drive, a flash memory drive, tape drives of various formats, USB device, hard-drive or any other device suitable for installing software and programs. The computing device 100 may further comprise a storage device, such as one or more hard disk drives or redundant arrays of independent disks, for storing an operating system and other related software, and for storing application software programs such as any program related to the software 120 for the demand side platform. Optionally, any of the installation devices 116 could also be used as the storage device. Additionally, the operating system and the software can be run from a bootable medium, for example, a bootable CD.

Furthermore, the computing device 100 may include a network interface 118 to interface to the network 104 through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, IEEE 802.11n, CDMA, GSM, WiMax and direct asynchronous connections). In one embodiment, the computing device 100 communicates with other computing devices 100' via any type and/or form of gateway or tunneling protocol such as Secure Socket Layer (SSL) or Transport Layer Security (TLS), or the Citrix Gateway Protocol manufactured by Citrix Systems, Inc. of Ft. Lauderdale, Fla. The network interface 118 may comprise a built-in network adapter, network interface card, PCMCIA network card, card bus network adapter, wireless network adapter, USB network adapter, modem or any other device suitable for interfacing the computing device 100 to any type of network capable of communication and performing the operations described herein.

In some embodiments, the computing device 100 may comprise or be connected to multiple display devices 124a-124n, which each may be of the same or different type and/or form. As such, any of the I/O devices 130a-130n and/or the I/O controller 123 may comprise any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may comprise multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices, such as computing devices 100a and 100b connected to the computing device 100, for example, via a network. These embodiments may include any type of software designed and constructed to use another computer's display device as a second display device 124a for the computing device 100. One ordinarily skilled in the art will recognize and appreciate the various ways and embodiments that a computing device 100 may be configured to have multiple display devices 124a-124n.

In further embodiments, an I/O device 130 may be a bridge between the system bus 150 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a FibreChannel bus, a Serial Attached small computer system interface bus, or a HDMI bus.

A computing device 100 of the sort depicted in FIGS. 1B and 1C typically operates under the control of operating systems, which control scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: Android, manufactured by Google Inc; WINDOWS 7 and 8, manufactured by Microsoft Corporation of Redmond, Wash.; MAC OS, manufactured by Apple Computer of Cupertino, Calif.; WebOS, manufactured by Research In Motion (RIM); OS/2, manufactured by International Business Machines of Armonk, N.Y.; and Linux, a freely-available operating system distributed by Caldera Corp. of Salt Lake City, Utah, or any type and/or form of a Unix operating system, among others.

The computer system 100 can be any workstation, telephone, desktop computer, laptop or notebook computer, server, handheld computer, mobile telephone or other portable telecommunications device, media playing device, a gaming system, mobile computing device, or any other type and/or form of computing, telecommunications or media device that is capable of communication. The computer system 100 has sufficient processor power and memory capacity to perform the operations described herein. For example, the computer system 100 may comprise a device of the IPAD or IPOD family of devices manufactured by Apple Computer of Cupertino, Calif., a device of the PLAYSTATION family of devices manufactured by the Sony Corporation of Tokyo, Japan, a device of the NINTENDO/Wii family of devices manufactured by Nintendo Co., Ltd., of Kyoto, Japan, or an XBOX device manufactured by the Microsoft Corporation of Redmond, Wash.

In some embodiments, the computing device 100 may have different processors, operating systems, and input devices consistent with the device. For example, in one embodiment, the computing device 100 is a smart phone, mobile device, tablet or personal digital assistant. In still other embodiments, the computing device 100 is an Android-based mobile device, an iPhone smart phone manufactured by Apple Computer of Cupertino, Calif., or a Blackberry handheld or smart phone, such as the devices manufactured by Research In Motion Limited. Moreover, the computing device 100 can be any workstation, desktop computer, laptop or notebook computer, server, handheld computer, mobile telephone, any other computer, or other form of computing or telecommunications device that is capable of communication and that has sufficient processor power and memory capacity to perform the operations described herein.

In some embodiments, the computing device 100 is a digital audio player. In one of these embodiments, the computing device 100 is a tablet such as the Apple IPAD, or a digital audio player such as the Apple IPOD lines of devices, manufactured by Apple Computer of Cupertino, Calif. In another of these embodiments, the digital audio player may function as both a portable media player and as a mass storage device. In other embodiments, the computing device 100 is a digital audio player such as an MP3 players. In yet other embodiments, the computing device 100 is a portable media player or digital audio player supporting file formats including, but not limited to, MP3, WAV, M4A/AAC, WMA Protected AAC, RIFF, Audible audiobook, Apple Lossless audio file formats and .mov, .m4v, and .mp4MPEG-4 (H.264/MPEG-4 AVC) video file formats.

In some embodiments, the communications device 101 includes a combination of devices, such as a mobile phone combined with a digital audio player or portable media player. In one of these embodiments, the communications device 101 is a smartphone, for example, an iPhone manufactured by Apple Computer, or a Blackberry device, manufactured by Research In Motion Limited. In yet another embodiment, the communications device 101 is a laptop or desktop computer equipped with a web browser and a microphone and speaker system, such as a telephony headset. In these embodiments, the communications devices 101 are web-enabled and can receive and initiate phone calls.

In some embodiments, the status of one or more machines 101, 106 in the network 104 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. Identifying a Material on a Body of a Person Using Electromagnetic Radiation

Described herein are systems and methods for identifying a material on a body of a person using electromagnetic radiation. The present systems and methods can be used to detect and/or identify material(s) (e.g., explosive materials) and object(s) that a subject may carry or wear. A subject may for example include a person or an animal. The material or object may be out of sight, for example, concealed under clothing. An electromagnetic system, such as a radar system, may be used to measure an electromagnetic response of radiation incident on a subject to perform scanning or probing. The system may recover or detect a geometrical profile or characteristic from the response. For example, the system may detect an electromagnetic excitation from a subject wearing explosive material or object under clothing. The electromagnetic excitation may cause or result in scattered or reflected field that the system may detect, collect, record and/or measure. The system may process data on the reflections or scattered field using one or more algorithms to detect and identify a material and/or object on or located proximate to the subject's body.

In some aspects, this disclosure addresses a problem of detecting potential suicide bombers wearing concealed metallic and dielectric objects. At present, radar may be the only modality that can penetrate and sense beneath clothing at a distance (e.g., 10 to 50 meters) without causing physical harm to a subject. In one illustrative embodiment, data produced by a Millimeter-Wave-Radar system for example, working on a Multiple Frequency-Multiple Transmitters and Multiple Receivers configuration (MF-MTMR), may be synthetically generated by an electromagnetic code based on a Finite Differences Frequency Domain (FDFD) method.

The numerical code may provide the scattered field produced by a subject under test, which may be processed by using a multiple bistatic Synthetic Aperture Radar (SAR) algorithm. Some of the blurring effects produced by a Point Spread Function (PSF) in the SAR image may be removed by applying a regularized deconvolution algorithm that uses magnitude information (e.g., no phase). The system can not only distinguish between materials, but is also capable of estimating the dielectric constant of a dielectric material. Each constitutive parameter can be directly mapped to a dielectric constant of known explosive compounds, such as TNT or RDX, making feasible the detection of potential suicide bombers.

Figure 2A:
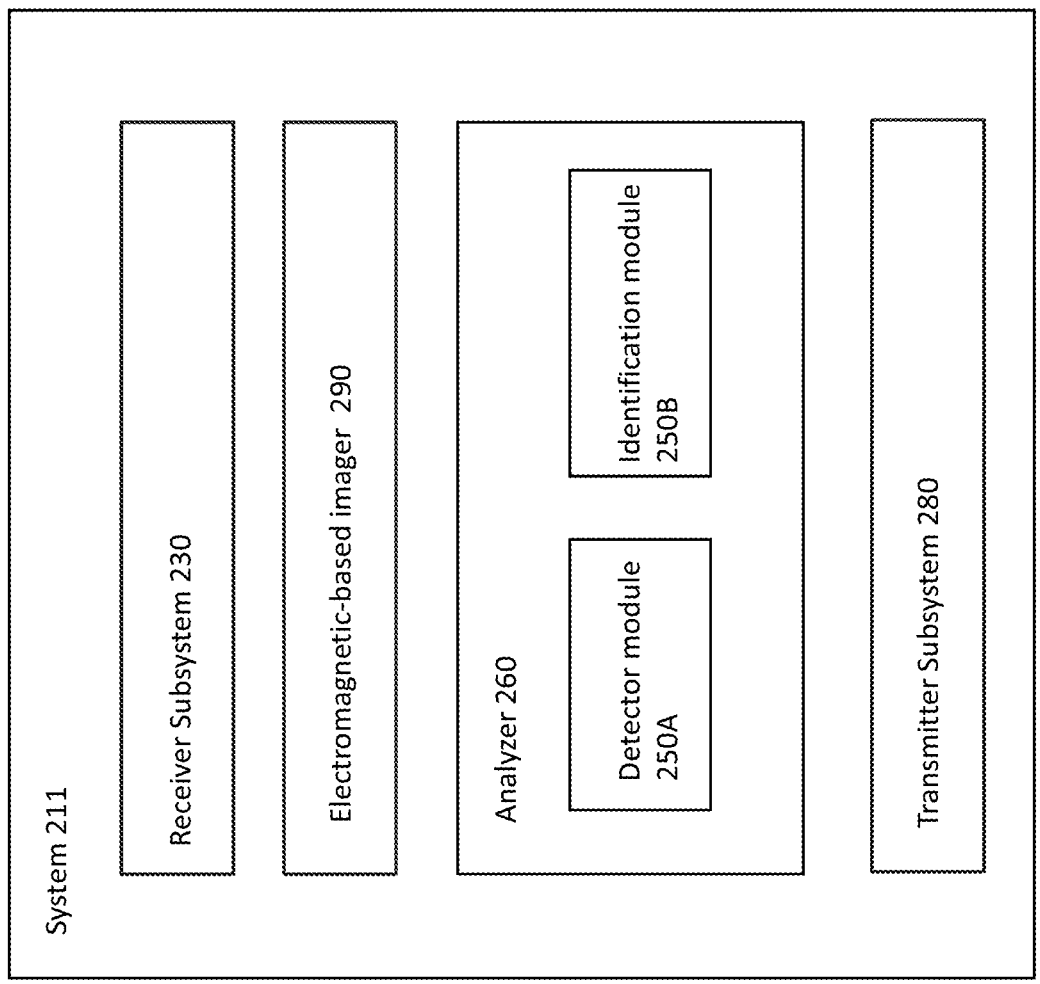
FIG. 2A is a block diagram depicting one embodiment of a system for identifying a material on a body of a person using electromagnetic radiation.
Figure 2A:
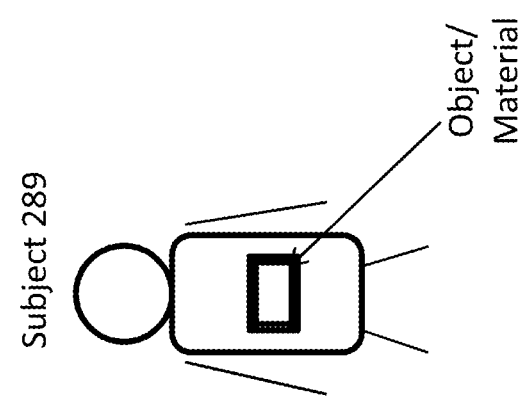

Referring to FIG. 2A, one embodiment of a system for identifying a material on a body of a person 289 using electromagnetic radiation is depicted. In brief overview, the system 211 may include one or more of a transmitter subsystem 280, a receiver subsystem 230, an electromagnetic-based imager for generating an image representing a scattered field from a subject 289, and an analyzer 260. The analyzer may include a detector module 250A for detecting an object or material on the body of the subject, and an identification module 250B for identifying the material or determining a dielectric constant of the material.

Figure 2B:
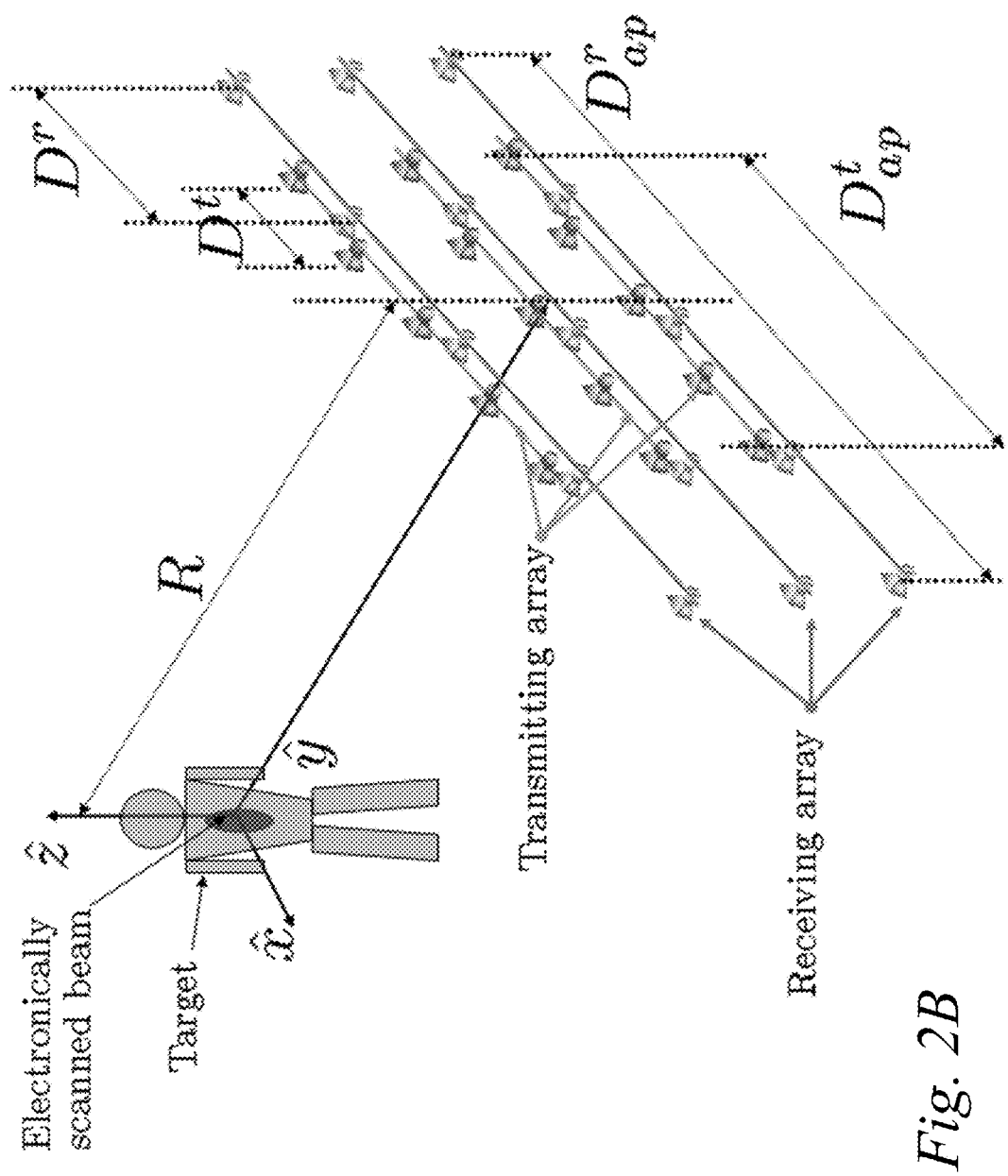
FIGS. 2B and 2C are diagrams depicting embodiments of a system for identifying a material on a body of a person using electromagnetic radiation.

In certain embodiments, the system includes a receiver subsystem for receiving or collecting the scattered field. The receiver subsystem may be configured to collect data for Multiple Frequencies, Multiple Transmitters and Multiple Receivers (MF-MTMR). The MF-MTMR configuration can include or be particularized to several types of radar configurations, for example 1) multiple monostatic, where a corresponding transmitter and receiver may be located on a same relative position with respect to each other for collected data; and 2) multiple bistatic configuration, where a corresponding transmitter and receiver may not be located on the same relative position with respect to each other for collected data. The system can operate in one or a plurality of frequency bands, including but not limited to microwave frequencies, millimeter wave frequencies, and Terahertz frequencies. By way of illustration, and as shown in FIG. 2B, one or more transmitter and receiver antennas of the system may be statically placed on a two-dimensional aperture, or can be moved to produce a synthetic aperture.

In some embodiments, and referring again to FIG. 2A, the system may include an electromagnetic-based imager. The electromagnetic-based imager may be integrated with, in communication with, and/or inter-operate with the receiver subsystem. Once data is collected by the receiver(s), the electromagnetic-based imager may use an imaging algorithm such as a phase-based imaging algorithm, to create or generate an image of an object of interest. The object of interest may include a subject and may include any peripheral material or objects that may be worn or kept with the subject, or otherwise attached to or embedded (e.g., partially embedded) on the subject. In certain embodiments, the system may include an analyzer to distinguish between different materials based on the image. The analyzer may detect or distinguish between any two or more of metallic, non-metallic, dielectric, organic, inorganic materials, for example.

By way of illustration for a security application, the electromagnetic-based imager may be used to distinguish between metallic and dielectric explosives. For the case in which a dielectric material has been detected, the analyzer may apply an algorithm to determine a dielectric constant of the dielectric material. As such, an explosive compound such as TNT or RDX, concealed under clothing by a potential suicide bomber, for example, may be detected and identified. The imager and/or the analyzer may measure a reflection produced on the surface of a dielectric material and a second retarded reflection produced on the surface of the person (e.g., interfacing with the material). The analyzer may determine a time delay in the second reflection relative to the first reflection. The analyzer may determine a delay in the first reflection relative to a reflection from a surface of the subject unobstructed by the material. The analyzer may determine a dielectric constant of the material based on at least one of the delays. In some embodiments, a particular dielectric constant value, or a range of dielectric constant values, may be mapped to a known explosive compound. The extent of retardation or delay due to propagation within each known material, can be pre-characterized and used by the system to identify a material.

The electromagnetic-based imager may generate an electromagnetic-based image, based on the detected or measured reflections or scattered field. By way of illustration, the electromagnetic-based imager may use or incorporate an imaging algorithm such as a High Resolution Phase-Based (HR-PB) imaging algorithm. The electromagnetic-based imager, or receiver subsystem, may include or employ one or more transmitters or radiation sources, and one or more receiving antennas or sensors. The electromagnetic-based imager may create the image by processing and/or assembling scattered field data received at the one or more antennas.

Figure 2C:
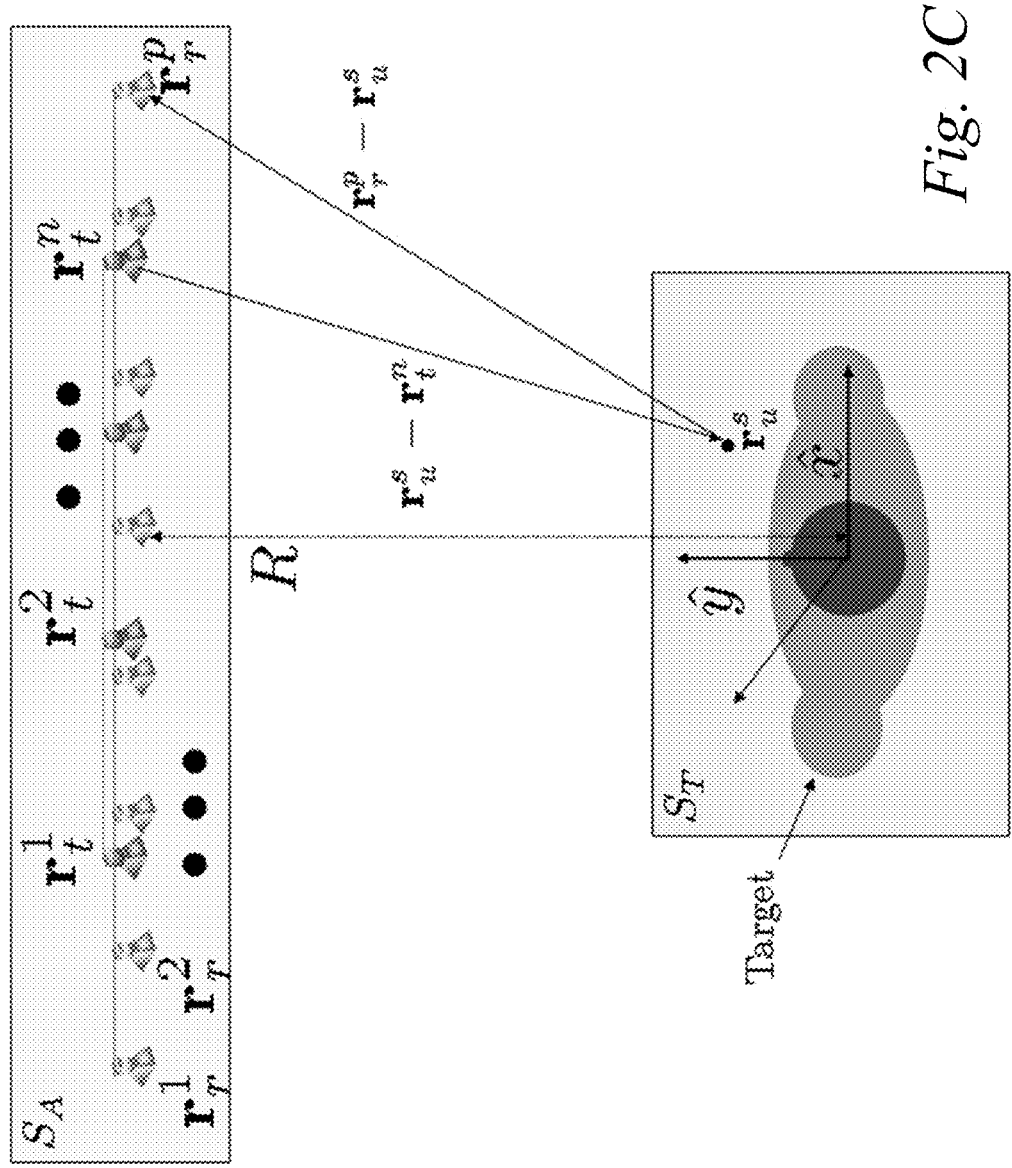

For example, in one embodiment using a multiple bistatic radar configuration, the electromagnetic-based imager may add a phase function to the fields, $E(f^l, r_t^n, r_r^p)$, measured on the p-th receiving antenna, located at $r_r^p$, when the n-th transmitting antenna, located at $r_t^n$, is radiating with the l-th frequency. FIG. 2C shows some of these aspects in a system for identifying a material on a body of a person using electromagnetic radiation. The phase function may depend on the imaging point $r_u^s$, and may be expressed in the following illustrative form:

$$\Phi_B^{FS}(f^l, r_t^n, r_r^p, r_u^s) = \phi_1 + \phi_2$$

$$\phi_1 = k_0^l |r_u^s - r_t^n|,$$

$$\phi_2 = k_0^l |r_r^p - r_u^s| \quad (1)$$

where $k_0^l$ may represent a wavenumber in free space for the l-th frequency. Based on this phase term, the HR-PB imaging functional at the point $r_u^s$ can be expressed as follows:

$$I(r_u^s) = \sum_{l,n,p} E(f^l, r_t^n, r_r^p) a(f^l, r_t^n, r_r^p, r_u^s) e^{j\Phi_B^{FS}(f^l, r_t^n, r_r^p, r_u^s)} \quad (2)$$

The coefficient $\alpha(f^l, r_t^n, r_r^p, r_u^s)$ may be an amplitude coefficient that can be considered constant, since the effect of the phase shift component may be dominant. With this formulation, rays scattered from objects arriving at the receiving array may have an appropriate phase shift to cancel a propagation path length phase, and thus constructively add, while rays from other points may randomly cancel. As such, points corresponding to scattering objects may appear bright in a darker background, due to the constructive addition.

TABLE 1

Parameters for the baseline configuration.

RADAR SOURCE

| | |
|---|---|
| Center frequency | $f_c$ = 94.5 [GHz] |
| Bandwidth | BW = 6 [GHz] |
| Number of frequencies | $N_t$ = 8 |
| Range resolution in air | ΔR = 0.0500 [m] |
| Grating lobes distance in range | $L^{t/r}$ = 0.7496 [m] |

TRANSMISSION
(equally spaced point sources)

| | |
|---|---|
| Number of transmitting antennas | $N_n$ = 13 |
| Position in [m] of the first element | $r_r^1$ = −0.35x + 10y |
| Position in [m] of the last element | $r_r^{13}$ = 0.35x + 10y |
| Cross range resolution in air | $\Delta R_x^t$ = 0.0454 [m] |
| Grating lobe distance in cross range | $L_x^t$ = 0.5459 [m] |

RECEPTION
(equally spaced point sources)

| | |
|---|---|
| Number of receiving antennas | $N_p$ = 13 |
| Position in [m] of the first element | $r_r^1$ = −1.6x + 10y |
| Position in [m] of the last element | $r_r^{13}$ = 1.6x + 10y |
| Cross range resolution in air | $\Delta R_x^r$ = 0.0099 [m] |
| Grating lobe distance in cross range | $L_x^r$ = 0.1192 [m] |

By way of illustration, one embodiment of a radar configuration is described in Table 1. The subject, e.g., a human subject, may be modeled based on a human cross section, which is represented in part (a) of FIG. 2D. Different regions of the cross-sectional image may be coded into a matrix of indices, as shown in part (b) for example. The matrix may be used by an electromagnetic field solver of the imager, such as a finite-different frequency-domain (FDFD) solver or an alternative solver. Part (a) may represent a real image of the human body cross-section, part (b) a FDFD model, and part (c) a FDFD model with metallic pipes. Parts (d) and (e) may represent embodiments of a SAR image and a cross section of a simulated human subject with no metallic pipes, and with metallic pipes, respectively.

The solver may generate synthetic data to be used by an algorithm of the imager. By way of example, and in one embodiment, free space may be represented by a certain value (e.g., a value of one) in the image, and the wave number at this region may be equal that of a wave propagating in free space. Skin may be coded by a value of zero, and the wave number corresponding to this region may be based on extrapolated measured dielectric constant values (e.g., at W-band). The solver may compute the fields in the first predetermined depth (e.g., 2 millimeters) of conducting high water content skin. The solver may consider the fields inside the human body to be zero, since the skin at working frequencies may be so conductive that waves may attenuate more than an order of magnitude by the time the waves traverse the skin layer. The latter approximation may reduce the computational cost of these analyses. Regions in which the total field is zero may be coded by a value of two in the image grid represented in part (b). By way of example, metallic pipes are also coded by a value of two in the image, since the total field may also zero at these regions, for example as shown in part (c) of FIG. 2D. Dielectric rods may be represented by adding an index to the grid, indicating a new dielectric wave number.

Figure 2D:
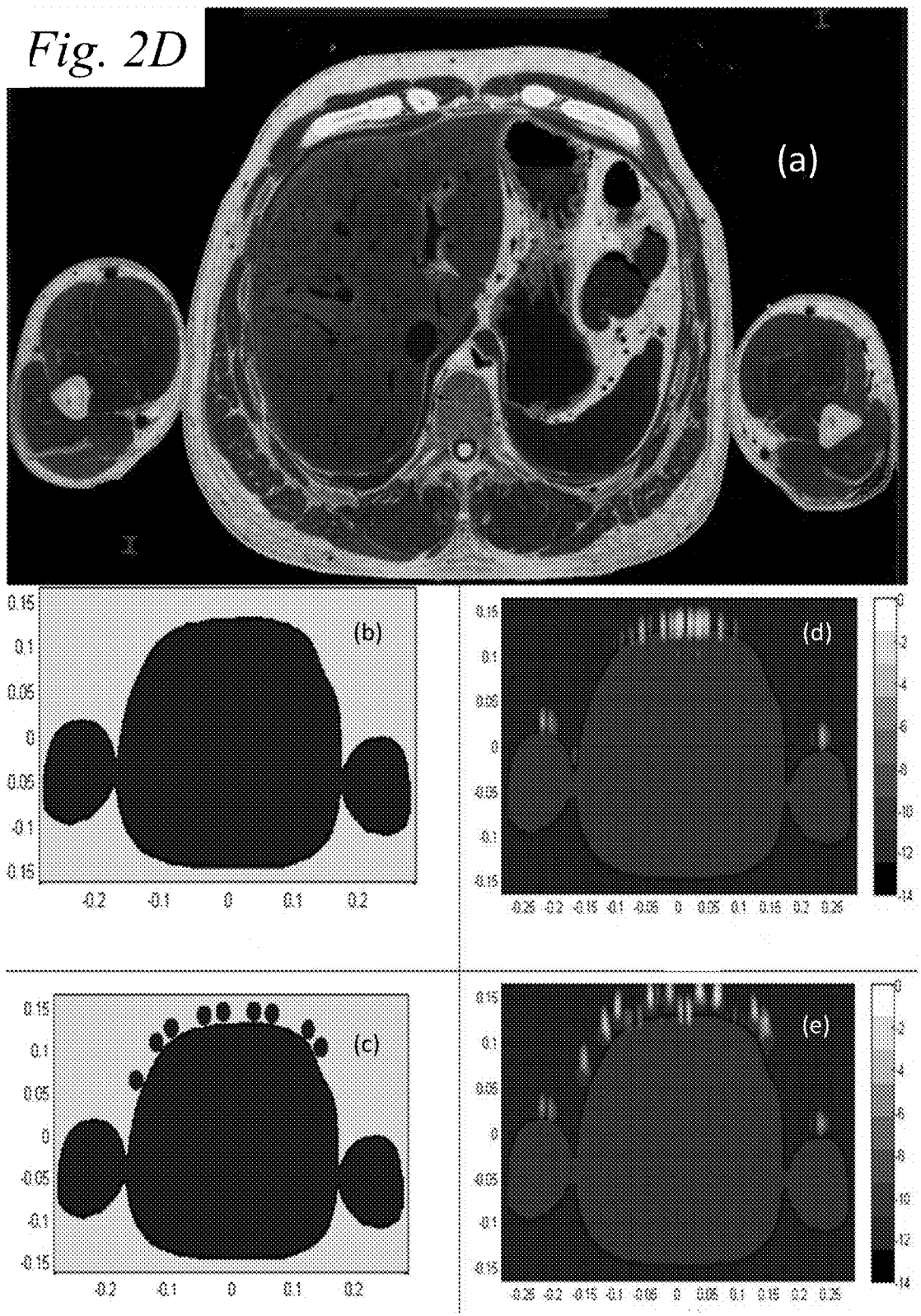
FIG. 2D comprises embodiments of images generated by the present methods and systems for identifying a material on a body of a person using electromagnetic radiation.

In some embodiments, images (e.g., HR-PB images) for a subject with and without accompanying metallic pipes may be illustrated by parts (d-e) of FIG. 2D. These images may be obtained from a pixel based matrix derived from the use of (2) and with the radar pointing normally to the front of the subject's torso, for example. In particular, part (d) may show the case of a person without accompanying metal pipes. The pixel intensity across the torso of the subject may present a relatively smooth variation in the image. Part (e) may illustrate an image for a person wearing a number of metal pipes. The pixel intensity across the torso may include abrupt variations mapping to the position of the metallic pipes. In these images, regions where a specular reflection contribution is produced can be observed in the images.

Figure 2E:
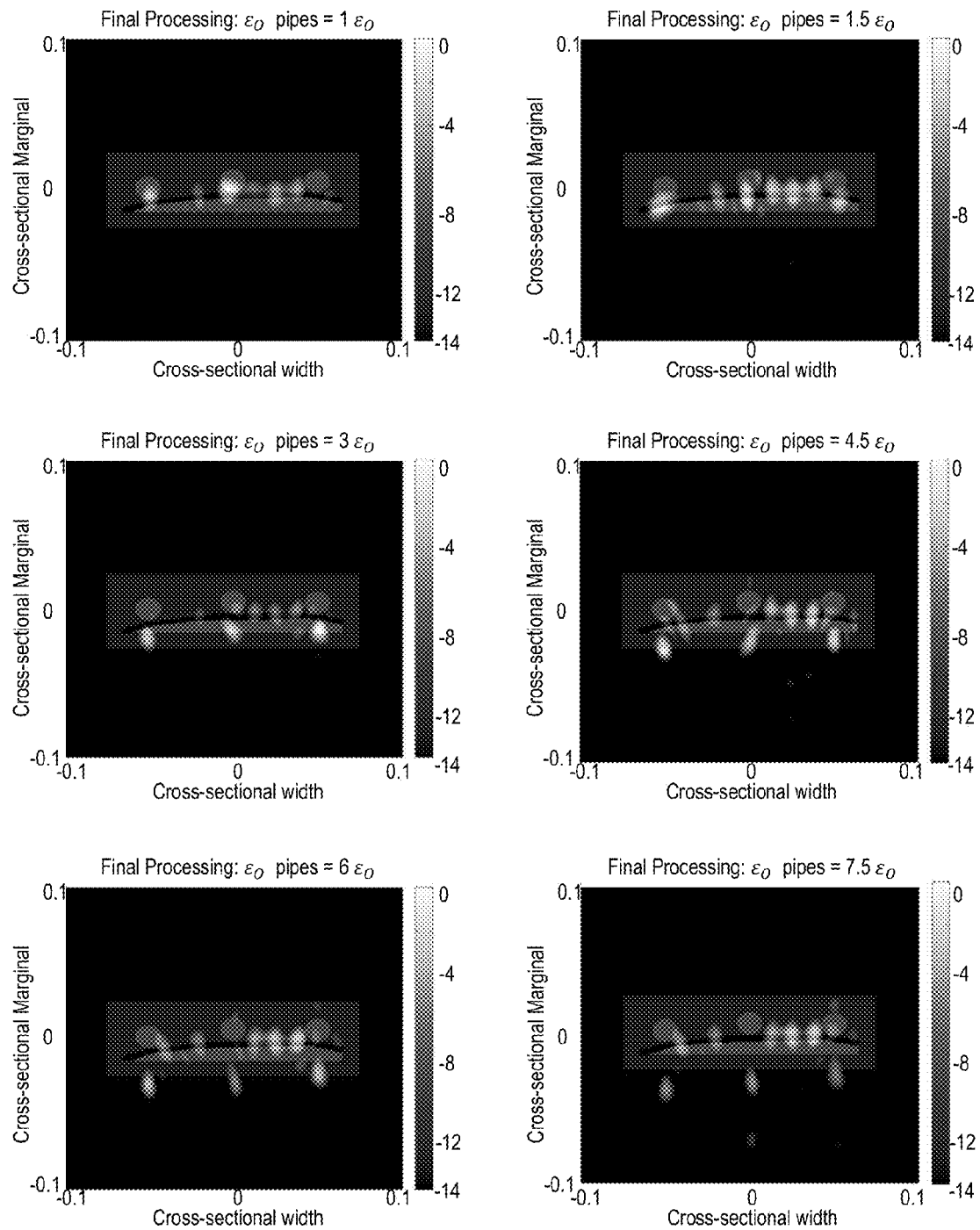
FIGS. 2E-2G comprise other embodiments of images generated by the present methods and systems for identifying a material on a body of a person using electromagnetic radiation.
Figure 2F:
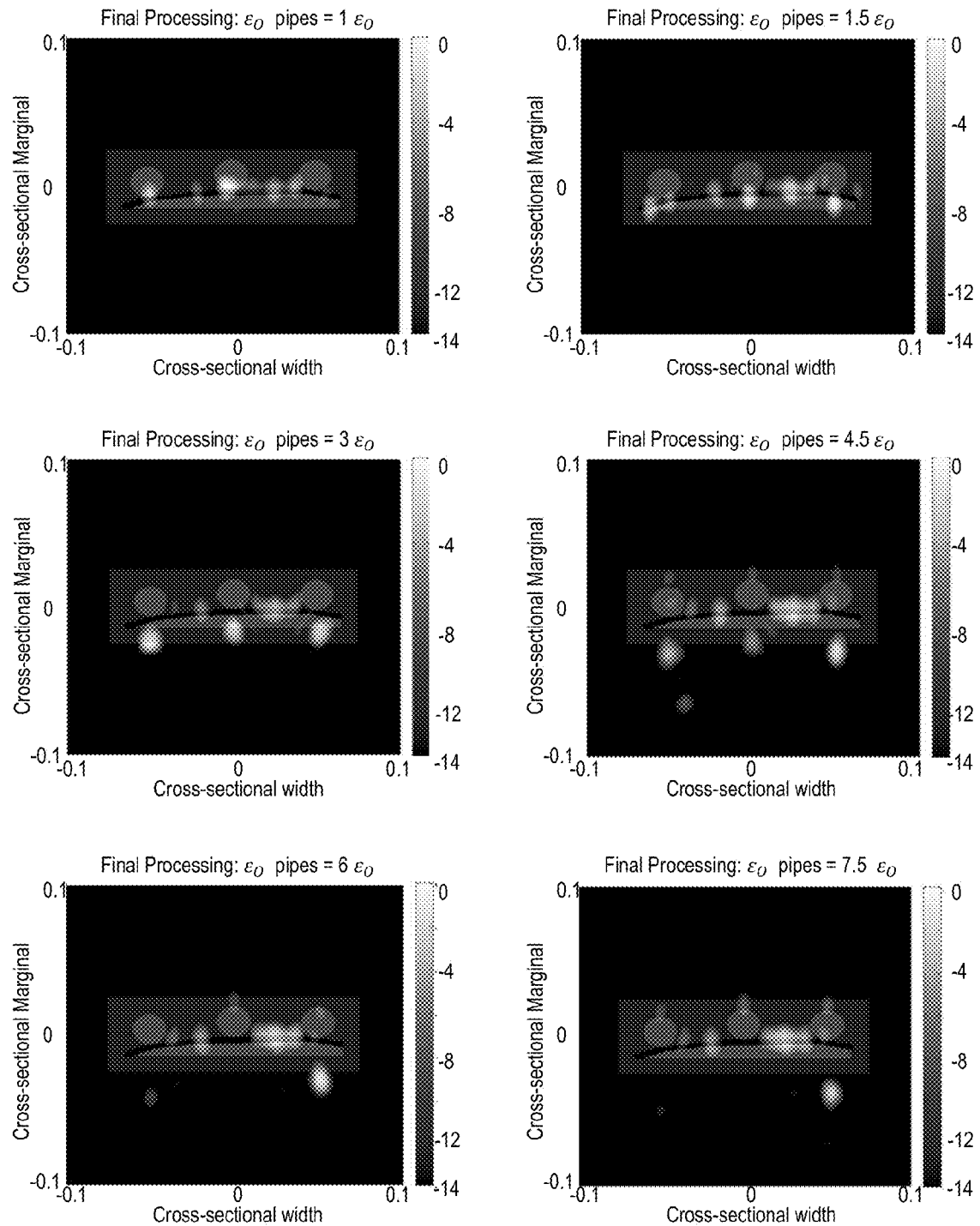
Figure 2G:
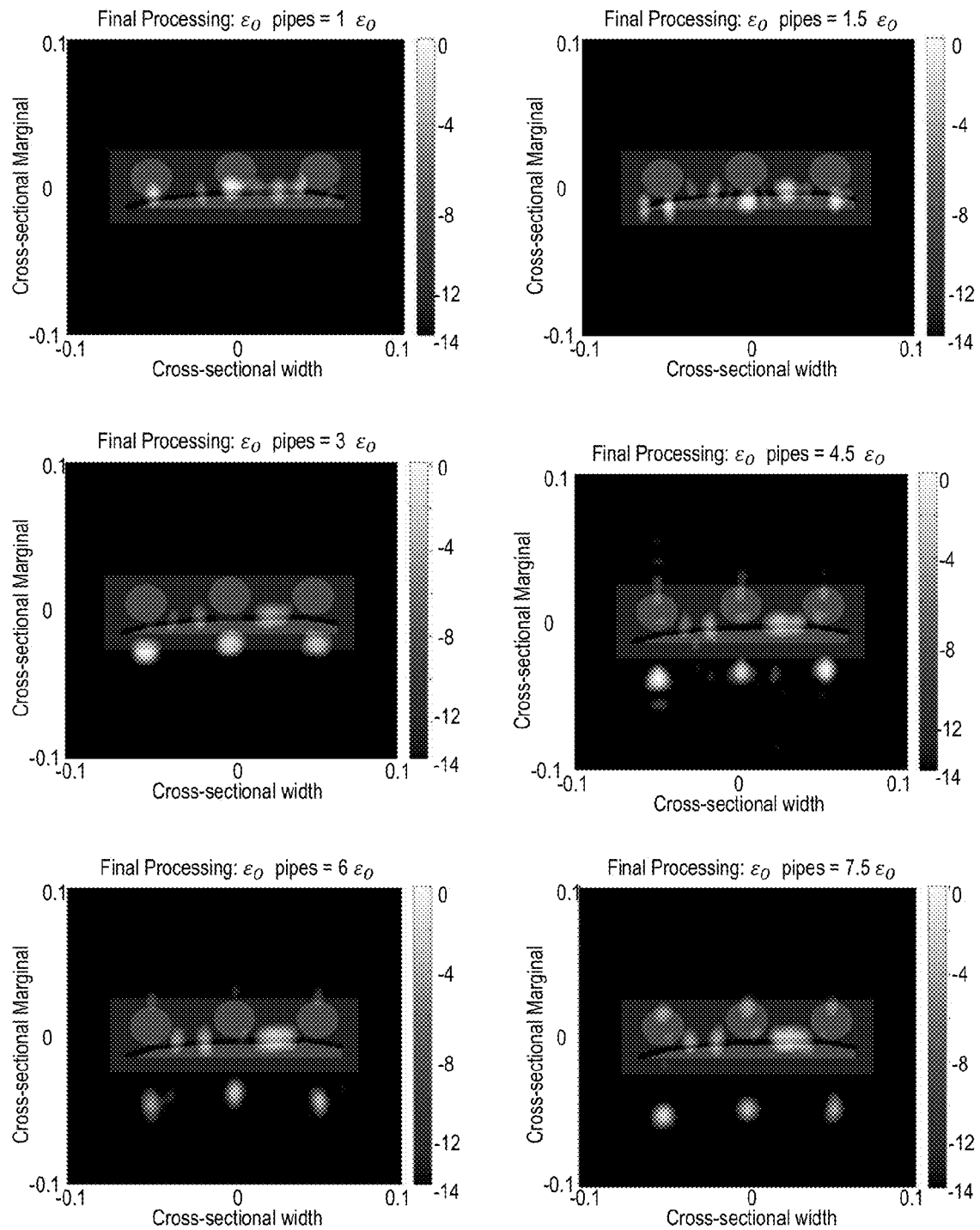

By way of illustration, FIGS. 2E-2G present embodiments of a front part of a human cross section region (which contains regions producing specular reflections) and the corresponding images when the diameter of the rods are 1.5, 2 and 2.5 [cm] and have different dielectric constants. Image pixel intensity may be identified against the intensity bars, which range from 0 to 14 dB; $\in_0$ is the free space dielectric constant.

In the case of metallic pipes, an image spot associated with each pipe may appear to be closer to the radar than the position of the pipe. In the case of dielectric rods, an associated spot may appear farther from the radar (e.g., radiation source) than an actual position of the rod relative to the subject's body. In some cases, a spot or reflection associated with a rod may appear to reside within the subject's body. The reason for this effect is that the imager may employ a process (e.g., a synthetic aperture radar or SAR algorithm) that images using the free space wavenumber in (2), but that the wavenumber for the field propagating through a dielectric rod is larger than the free space wavenumber. Therefore, the speed of propagation in the dielectric may be reduced, and the spot associated with the dominant reflection from the chest (e.g., interfacing with or proximate to the rod) may be delayed. When the relative permittivity of the dielectric rod is increased, the velocity may be further reduced, and the delay for the chest reflection spot may also increase, making the spot appear deeper into the chest. As such, images generated by the imager may be analyzed visually by a user or by a detector module executing an algorithm, to check if an unknown object or material on a subject may be metallic or dielectric. Metallic threats may be detected by identifying abrupt variations on an HR-PB image. Dielectric threats may be detected by identifying spot retardations on an HR-PB image.

In some embodiments, the system's analyzer may include an identification module. The identification module may perform dielectric constant characterization of a detected dielectric material. The identification module may operate on the same image generated by the imager, e.g., an HR-PB image. In some aspects, the pixel intensity in the image may be proportional to electric currents coinciding with that pixel. If the material placed in the pixel under study is a good conductor (e.g., no energy penetrates in the material under test), reconstruction of the currents according to (2) may provide an estimation of the position of the currents in the domain. Thus, a shape of the object may be estimated with an accuracy given by the resolution of the radar system.

Figure 2H:
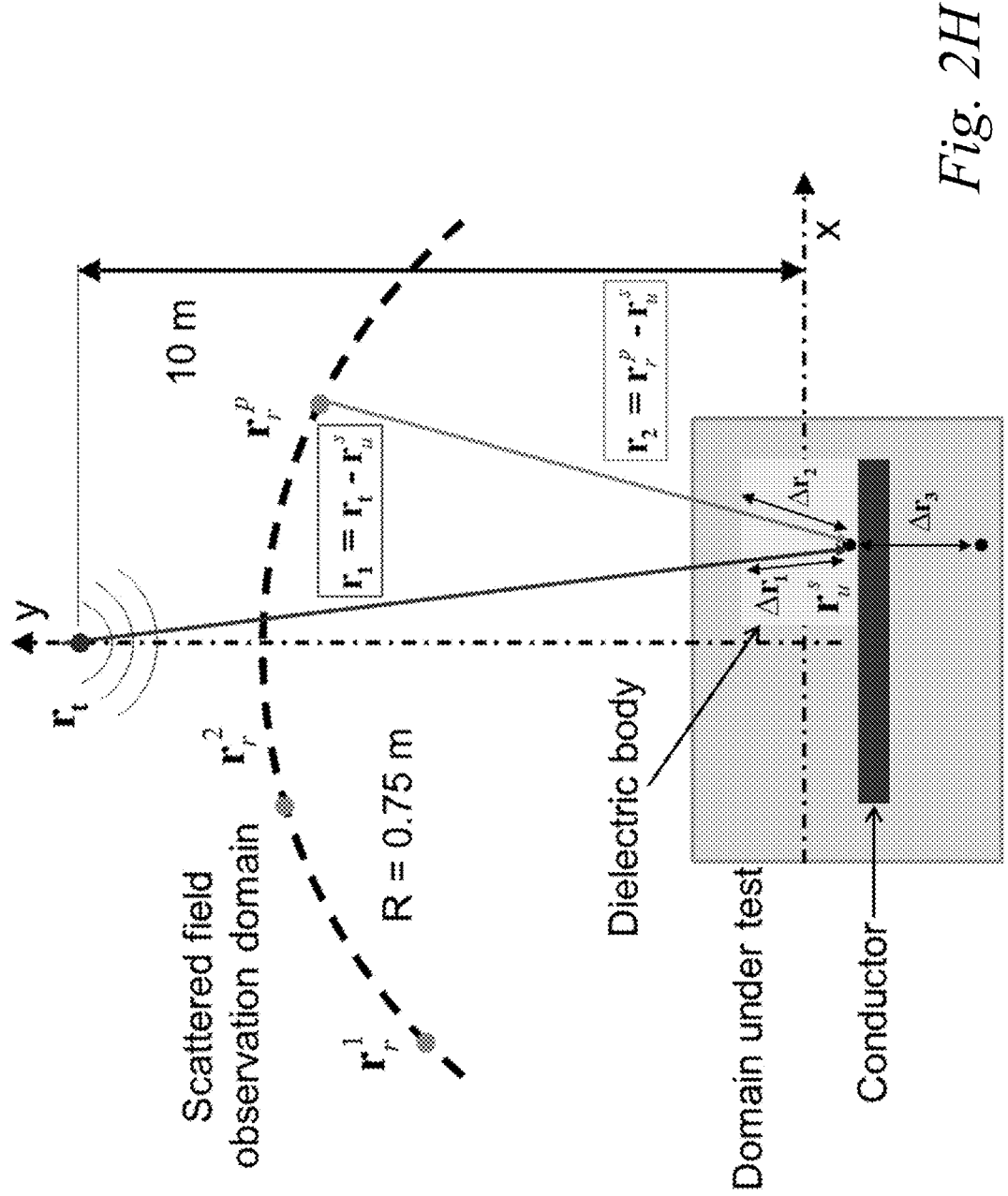
FIG. 2H comprises a scheme for identifying a material on a body of a person using electromagnetic radiation.

However, in the case of a dielectric material, a certain amount of energy proportional to the transmission coefficient between the air and the dielectric may propagate through the material. In some embodiments, the wavenumber for this propagating field may be expressed by $k_d^1 = 2\pi f^1 \sqrt{\mu_0 \in_r \in_0}$, where $\in_r$ is the relative dielectric constant of the dielectric material. As such, the speed of propagation in the dielectric may be reduced with respect to the speed in air. In some embodiments, the current imaged on a point placed on the surface of the obstructing conductor, $r_u^s$ for example as shown in FIG. 2H, may be expressed in (3):

$$I(r_u^s) = \sum_{l,p} \left\{ \begin{array}{l} E(f^l, r_t, r_r^p) \cdot \\ \cdot e^{+jk_0^l(|r_1|-|\Delta r_1|+|r_2|-|\Delta r_2|)+jk_d^l(|} \end{array} \right. \quad (3)$$

The difference between the phase terms of (3) and (1) may provide the following phase term error for a given l-frequency and p-position:

$$\frac{I(r_u^s)|_{Dielectric}^{l,p}}{I(r_u^s)|_{Free\,space}^{l,p}} = \frac{e^{+jk_0^l(|r_1|-|\Delta r_1|+|r_2|-|\Delta r_2|)}}{e^{+jk_0^l(|r_1|)}} \quad (4)$$

$$= e^{+jk_0^l(-|\Delta r_1|-|\Delta r_2|)+jk_d^l(|\Delta r_1|+|\Delta r_2|)}$$

$$= e^{-jk}$$

The phase term error introduced in the reconstruction (4) may displace the position of the currents in the image to a distance $|\Delta r_3|$ that can compensate the phase and add the currents in phase error when:

$$\sum_{l,p} e^{jk_0^l 2|\Delta r_3|} = \sum_{l,p} e^{-jk_0^l(|\Delta r_1|+|\Delta r_2|)(1-\sqrt{\varepsilon_r})} \quad (5)$$

$$= \Rightarrow 2|\Delta r_3|$$

$$= (|\Delta r_1|+|\Delta r_2|)(\sqrt{\varepsilon_r}-1)$$

This effect may not be taken into account in the HR-PB formulation in (1) since the wavenumber in free space may be used to reconstruct the currents on each pixel of the image. However, it can be used to identify the dielectric constant of the material under test. The fact of using the free space wavenumber in the HR-PB processing can create the effect of displacing the reflection on the obstructed surface of the conductor an amount $|\Delta r_3|$ in the approximate direction of the incident wave. Since this displacement may be directly proportional to the dielectric permittivity and size, its identification in the image can provide information on the dielectric body permittivity and size (e.g., thickness or depth).

A maximum amplitude or intensity value in the generated image may correspond to a position where the incident field is reflected back from (i) the surface of the dielectric object, or (ii) the skin of the human person. The distance between the conductive skin and the dielectric surface is $d_{obj}$; and the distance between the conductive skin and the position of the retarded spot is $d_{echo}$. If these two measurements can be inferred, measured, extracted, or otherwise determined from the image, the dielectric constant of the material can be determined by using the following equation:

$$\varepsilon_{r,est} = (1+(d_{echo}/d_{obj}))^2 \quad (6)$$

Figure 2I:
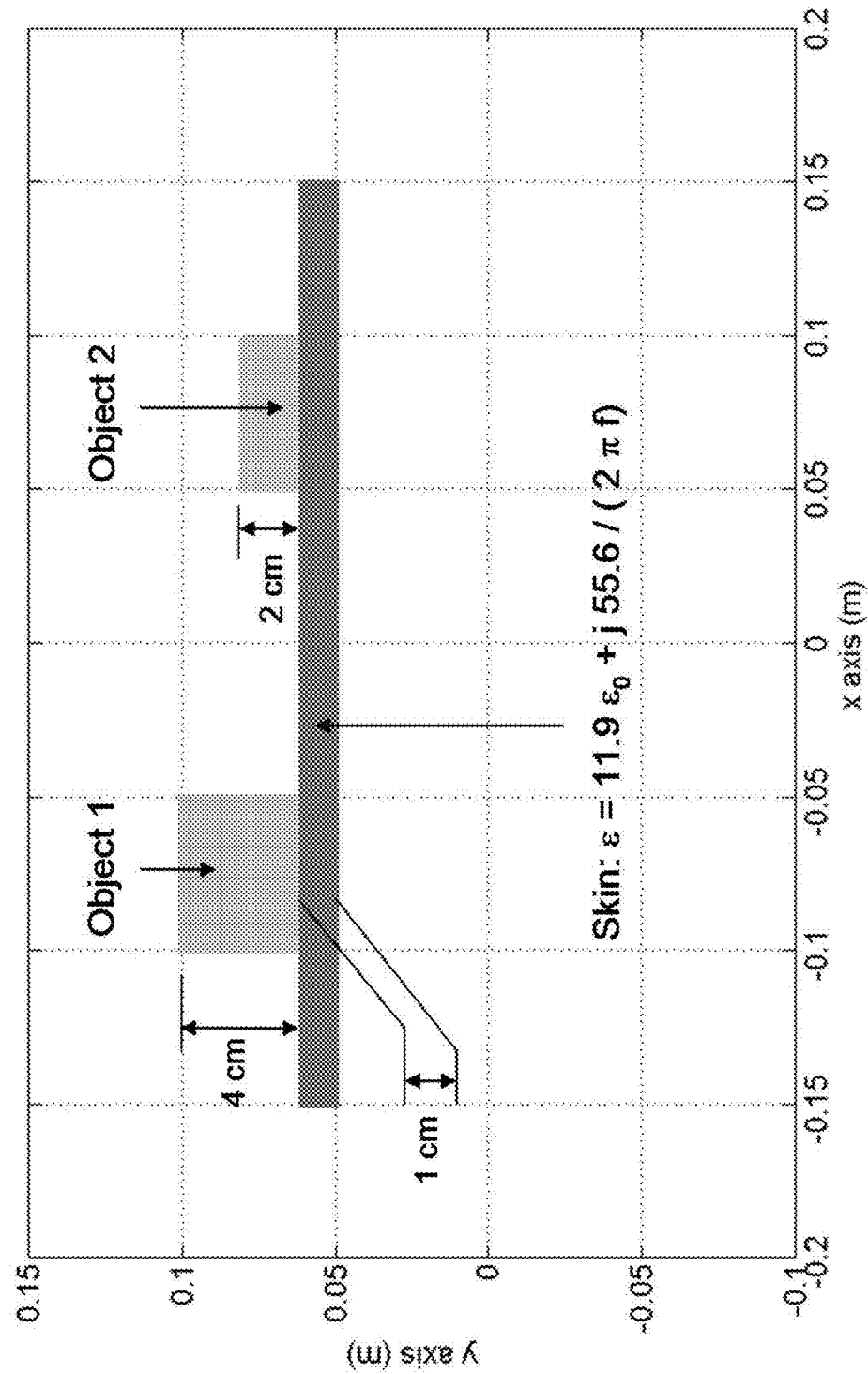
FIG. 2I comprises one embodiment of a system for identifying a material of each of two object on a body of a person using electromagnetic radiation.

By way of illustration, the following is a numerical example of dielectric constant characterization of an explosive material. For this particular example, the frequency bandwidth of the radar may be 15 GHz, running from 55 to 70 GHz in 500 MHz-steps (e.g., a bandwidth of 24% with respect to the center frequency, 62.5 GHz). A scenario for a test subject may be simulated or modeled using a Frequency Domain Finite Differences (FDFD) algorithm. Two dielectric objects may be placed on a 1-cm thick skin slab, for example as shown in FIG. 2I. At the considered working frequency band, the skin may behave almost as a perfect electric conductor (PEC) due to the high water content of the human body. Under these conditions, a 1 cm thickness may be a good approach for the skin. The scenario is analyzed for different values of the relative dielectric constant of the bodies to show the behavior of the SAR system in terms of permittivity and shape identification.

Figure 2J:
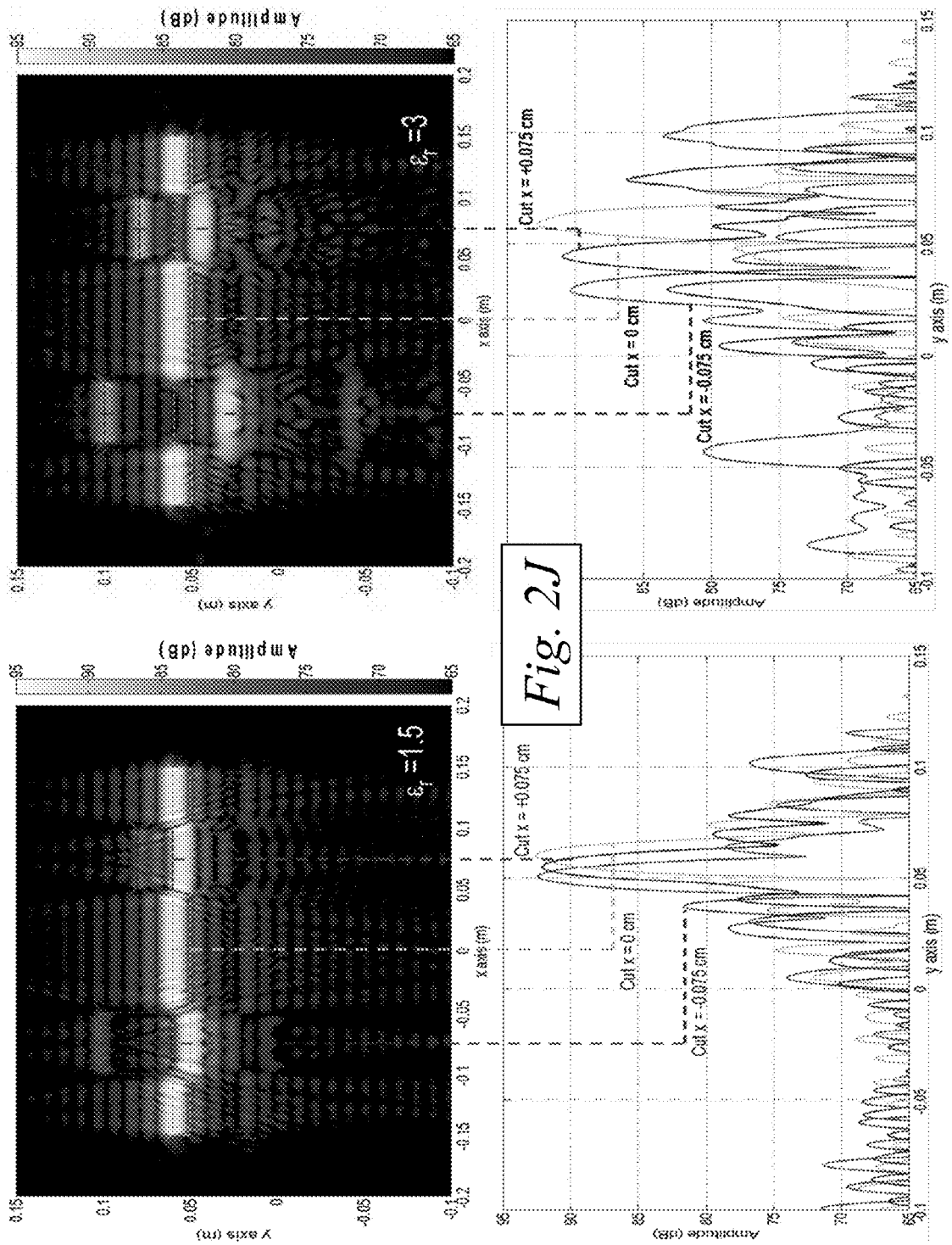
FIGS. 2J-2K comprise yet other embodiments of images generated by the present methods and systems for identifying a material on a body of a person using electromagnetic radiation.
Figure 2K:
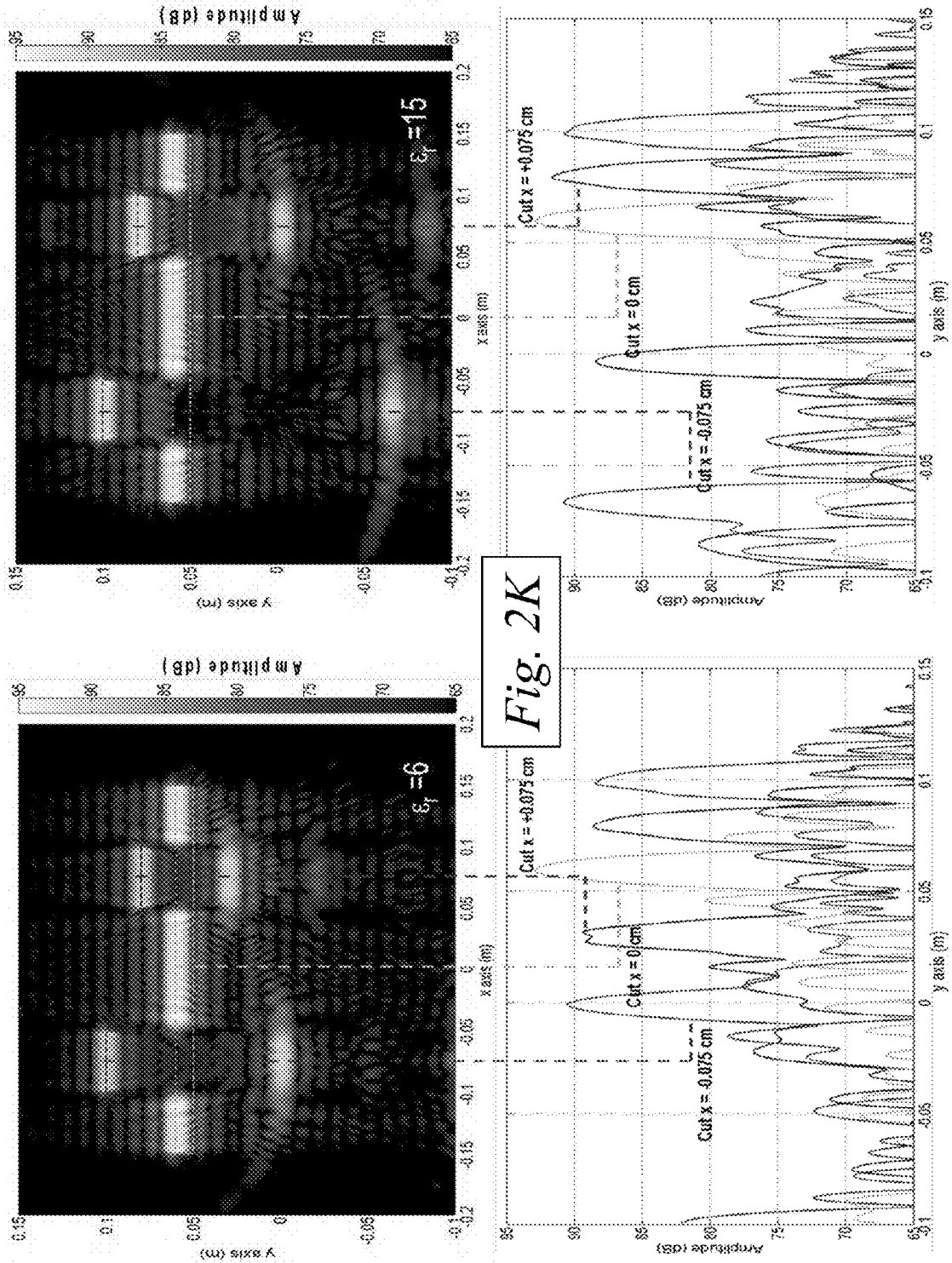

In this example, the selected geometry is illuminated by a cylindrical wave centered at $(x,y)=(0,10)$ m. The back-scattered field on a 180°-arc, placed R=0.75 m away from the geometry-under-test is calculated. The sampling rate is $\Delta\phi=1.25°$, which is about $0.5\lambda$ at the center frequency. From the scattered field, the equivalent currents are retrieved on a $0.4\times0.25$ m domain, sampled each $\Delta S=(0.1\lambda)^2$. The retrieved SAR images for different constitutive parameters values are plotted in FIGS. 2J and 2K. Several cuts in the line perpendicular to the dielectric center are presented to show the maximum reflection points for different dielectric objects. For example, cuts along y-axis for different dielectric constants: (a) $\varepsilon_r=1.5$, (a) $\varepsilon_r=3$, (a) $\varepsilon_r=6$, and (a) $\varepsilon_r=15$, are shown in FIGS. 2J and 2K.

Figure 2L:
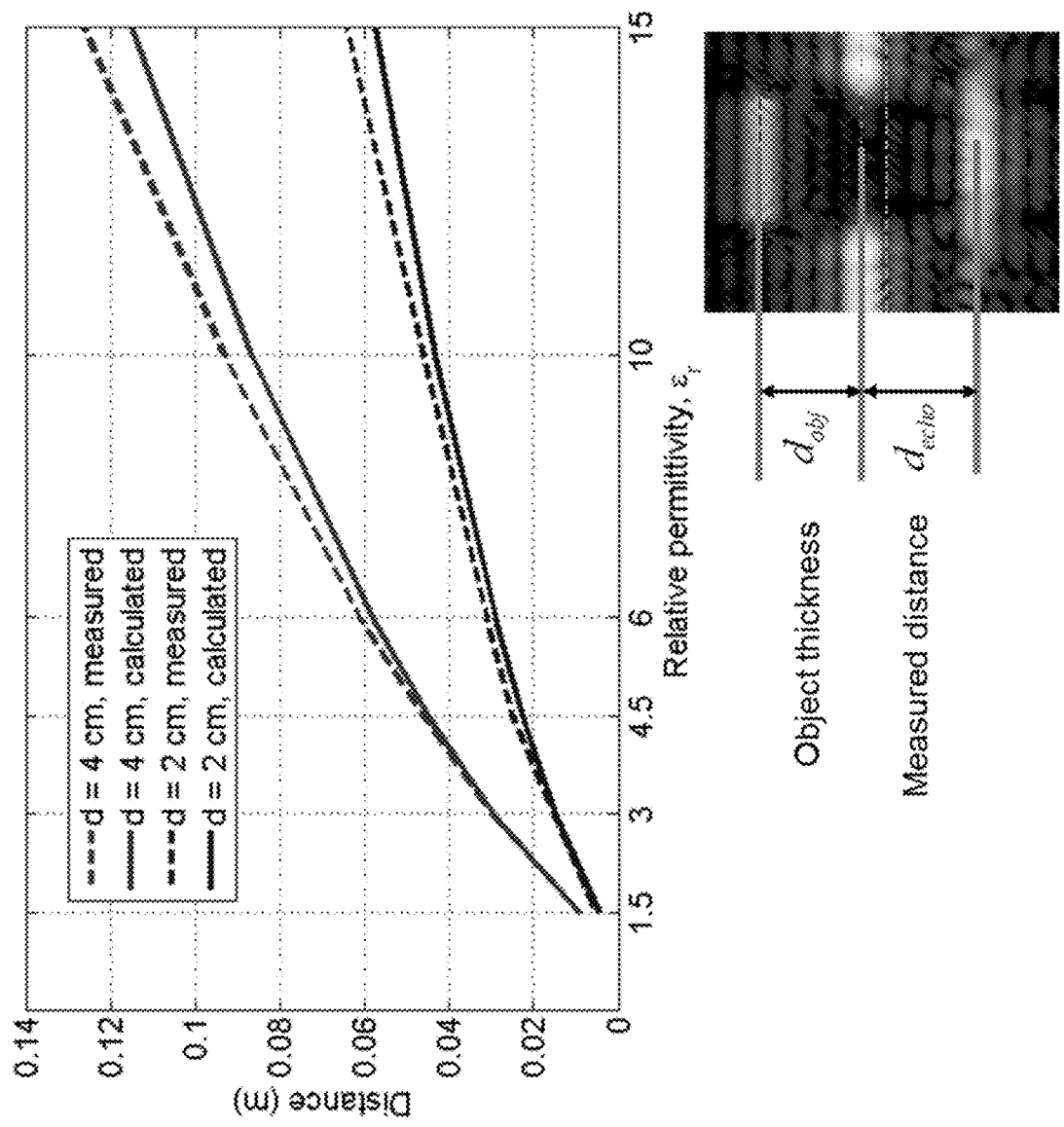
FIG. 2L shows one embodiment of an object thickness and measured distance, as determined from an image, as compared to calculated values.

In some embodiments, the values of $d_{obj}$ and $d_{echo}$ can be inferred from the image, and the dielectric constant can be determined from (6). FIG. 2L shows one embodiment of the object thickness and measured distance, as determined from an image. FIG. 2L also provides details of calculated and measured distances at which the echo due to the reflection between the dielectric and skin interfaces is located. As such, the identification module of the analyzer can identify a value of the dielectric constant of the explosive threat. The system can use the dielectric constant to identify the type of material (e.g., explosive) being worn by the subject under analysis (for example, TNT has a $\varepsilon_r=3$). Both the detector and identification modules have been validated using measured data instead of using synthetic data generated by a numerical model such as FDFD.

Former and other approaches for millimeter wave imaging are traditionally based on Fast-Fourier-Transforms (FFT) of the measured data. Some disadvantages of such types of systems may include the following:

1. The typical Fourier-Based type of processing only works for multiple-monostatic configurations. For this configuration, the transmitter and receiver antenna are located close to each other and only one measurement is collected for each angular illumination of the target.
2. In order to apply FFT processing, the data are sampled uniformly in the space and frequency domains, and the separation between antennas should be less than half a wavelength. Thinned arrays are not used for FFT processing because they do not sample the scattered field at the required half a wavelength.
3. In order to apply FFT processing, the transmitting/receiving antenna is mechanically moved in order to collect the required data. This sampling requirement makes the data collection a slow process.
4. Traditional Millimeter Wave Imaging algorithms does not consider that the explosive simulants may be located on the surface of the person under test; and, therefore, the characteristic electromagnetic interaction and signature between the dielectric structure and the person under test are not used to help determine the dielectric constant of the explosive simulant. Most of the Fourier-Based imaging algorithms have been developed for military purposes since 1950. These imaging algorithms were oriented to work with data that was collected in the far-field region of the radar; and, in general, no a-priori information about the target shape or orientation was considered by these imaging algorithm In some aspects, the present systems and methods recognize that concealed materials such as explosive simulants, may be located on or close to the skin surface of a subject. Characteristic electromagnetic signatures for this configuration, based on beam retardation for dielectric materials and abrupt variations for metallic materials, may be extracted from the reconstructed image generated by the present imager. These signatures can be used to determine the constitutive parameters of an explosive simulant.

In some embodiments, the present systems and methods can operate with multiple-bi-static configurations. For this configuration, the transmitter and receiver antenna are not located close to each other and multiple measurements are collected for each angular illumination of the target. The present systems and methods can process data that may have been collected in a non-uniform way, in both the spatial and frequency domains. Therefore, thinned arrays can be used to collect the scattered data, and the antennas do not have to be separated by one half wavelength. The present systems and methods can process multiple bi-static data. As a result, information can then be collected for a single transmitter and multiple receivers in a short period of time, and no movement of the antennas in the system may be required. These less restrictive sampling requirements can speed up the data collection process. The present systems and methods can account for the fact that the explosive simulants may be located on the surface of the person under test. As a result, the characteristic electromagnetic interaction and signature between the dielectric structure and the person under test may be used to infer the dielectric constant of the detected material.

In some embodiments, the present systems and methods can account for the attenuation factor derived from the conductivity component on the dielectric constant. The imager can account for this component to provide an even more accurate dielectric characterization of the explosive simulant. Additionally, in some embodiments, the output of the system can be incorporated to a fast forward method to have another validation of the estimated dielectric constant. The present systems and methods can be incorporated into present security systems, e.g., at security checkpoints, without requiring any or significant hardware modification on the present systems. This can make a transition into the field very fast, and can substantially contribute to increased detection rates and identification capabilities.

The present systems and methods can be used on millimeter wave imaging systems that are customized to work on whole body or partial body imaging applications, for example, on near-field distances (e.g., less than 2 meters). Certain embodiments of the present systems and methods can be applied at standoff ranges (e.g., 10-50 meters) or at other ranges, and may be suitable for the detection of potential suicide bombers.

Figure 2M:
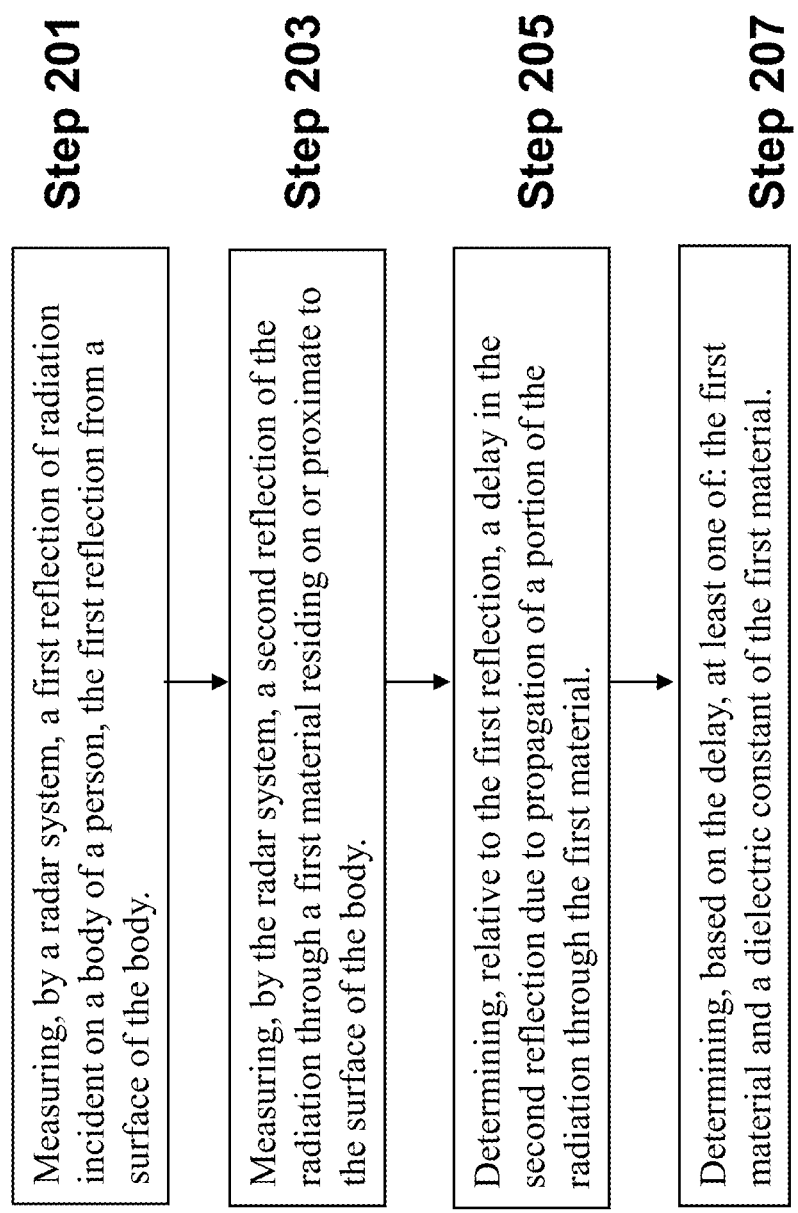
FIG. 2M is a flow diagram of an embodiment of a method for identifying a material on a body of a person using electromagnetic radiation.

Referring now to FIG. 2M, one embodiment of a method for identifying a material on a body of a person using electromagnetic radiation is depicted. The method may include measuring, by a radar system, a first reflection of radiation incident on a body of a person (201). The first reflection may be from a surface of the body. The radar system may measure a second reflection of the radiation (203). The second reflection may be through a first material residing on or proximate to the surface of the body. An analyzer may determine, relative to the first reflection, a delay in the second reflection due to propagation of a portion of the radiation through the first material (205). The analyzer may determine, based on the delay, at least one of: the first material and a dielectric constant of the first material (207).

Referring now to (201), and in some embodiments, a radar system may measure a first reflection of radiation incident on a body of a person. The first reflection may be from a surface of the body. The radar system may provide one or more transmitters for providing incident electromagnetic radiation, and one or more receivers for receiving or detecting reflections or a scattered field based on the provided electromagnetic radiation. The radar system may detect, monitor and/or scan a subject for possible objects or materials worn on or carried with the subject. The radar system may employ electromagnetic radiation to scan, probe, or otherwise check a subject for possible unknown or hidden objects or materials. For example, and in some embodiments, the radar system may include one or more sources (e.g., a point source) for millimeter wave radiation. The radar system may include an array of detectors (e.g., arranged in one dimension), which may move relative to a subject to measure or detect components of the scattered field (e.g., in two dimensions).

By way of illustration, the radar system may incorporate a MF-MTMR configuration, for example as described above in connection with FIG. 2A, for scanning or collecting data from a subject. In certain embodiments, the radar system may provide a multiple monostatic or multiple bistatic configuration for scanning or collecting data from a subject. The radar system may orient or position itself (e.g., the one or more transmitters and receivers), relative to the subject. The radar system may guide or instruct the subject for positioning the subject relative to the radar system. The radar system may detect motion in the subject and may perform positioning and/or scanning in relation to the motion. The radar system may perform scanning or checking responsive to a known or potential security or safety threat, or as part of an surveillance or access control measure. The radar system may perform scanning or checking over one or more radiation frequencies, for example, to leverage on frequency diversity and/or reduce interference between transmitters or receivers, or interference with another source.

In certain embodiments, the radar system may provide or direct radiation to be incident on a body of a subject. The radar system may detect, monitor or otherwise measure a reflection of the radiation. The radar system may measure a reflection from a surface of the body, using one or more spatially distributed detectors or sensors. The radar system may measure a reflection from an exterior and/or at least partially conducting surface of the body. For example, the radar system may measure the reflection from a skin, scalp, or another part of the body. The radar system may measure the reflection from the a region or portion of the body surface unobstructed or substantially unobstructed by an object or material. For example, the radar system may measure the reflection from radiation transmitted through clothing, garment material, fibers, fur, hair, or a layer of material below a predefined thickness, density and/or permittivity, on the subject.

In some embodiments, a reflection or field measured by a detector or sensor of the radar system may be stored or processed in relation with a location of detector/sensor and/or a location of the corresponding region of the body surface. The reflection may be received or measured earlier or later than another reflection from the same region or a nearby region. The radar system may determine that the reflection has not been delayed or substantially delayed by an object or material along the path of the reflection and corresponding incident wave.

Referring now to (203), and in some embodiments, the radar system may measure a second reflection of the radiation through a first material residing on or proximate to the surface of the body. The radar system may measure a reflection or scattered field from another region or portion of the surface of the body. The radar system may measure a reflection or scattered field from another region close to or proximate to a region corresponding to the first reflection. The radar system may detect or determine that the reflection is from a region of the surface close to that of the first reflection. The radar system may measure a reflection from a region of the surface close to that of the first reflection. The radar system may detect or determine that the reflection is significantly delayed (e.g., above a predefined threshold) relative to the first reflection. The radar system may measure the second reflection using one or more detectors/sensors different from a detector/sensor that measured the first reflection.

In some embodiments, the radar system may detect a presence of an object or material in the path of the reflection or incident wave. For example, another reflection (e.g., a third or partial reflection, from a surface of an intervening object or material) may be detected prior to a reflection (e.g., partial reflection) from a surface of the subject's body. In some embodiments, another reflection from a surface of an intervening object or material, adjacent to (or interfacing with) the surface of the body, may be detected. In certain embodiments, the second reflection may comprise or incorporate at least a portion of the latter reflection.

By way of explanation and in some embodiments, a portion of the incident radiation may be obstructed by an object or material (e.g., other than clothing). The material may comprise a dielectric material (e.g., an explosive substance). A portion of the radiation may be reflected off the exterior or outward-facing surface of the material. A portion of the radiation may transmit or propagate through the material, towards a surface of the body beneath or behind the obstructing material. A portion of the transmitted radiation may be reflected off a surface of the material (e.g., partial internal reflection within a medium) without emerging from the material to be incident on the surface of the body. In some embodiments, the latter surface may be located close to or against a surface of the body. For example, concealed explosives may be strapped tightly or closely against a person's body. A portion of the transmitted radiation may be reflected off the surface of the body, e.g., back into the material. A significant portion of the latter reflection may transmit into the material and/or propagate through the material. A significant portion of the propagated reflection may emerge from the material and be detected or measured by the radar system (e.g., as the second and/or delayed/retarded reflection).

The radar system may include an electromagnetic-based imager, such as one employing a phase-based imaging algorithm (e.g., HR-PB algorithm), for example as described above in connection with at least FIG. 2A. The imager may process data collected or measured by the detectors or sensors, including the first and second reflections. The imager may generate an image of the subject and/or reflections measured by the radar system. The imager may generate an electromagnetic-based image identifying the first reflection and the second reflection. The imager may generate a two or three dimensional image of the subject and/or reflections measured. The imager may generate images representing one or more of the reflections, e.g., in relation to a location or mass of the subject and/or a detected object or material. The imager may generate images representing one or more of the reflections, to identify a location or mass of the subject and/or a detected object or material. The imager may generate image features corresponding to a scattering object (e.g., an object or material, or the body of the subject) using phase-based constructive addition.

Referring now to (205), and in some embodiments, an analyzer may determine, relative to the first reflection, a delay in the second reflection due to propagation of a portion of the radiation through the first material. Radiation propagating through the material may be delayed along the direction towards the surface of the body, and/or upon reflection along the direction away from the surface of the body. The relative permittivity of the material is higher than that of air or free space, and thus causes a reduction in the propagation velocity of a field through the dielectric material. When the relative permittivity of the dielectric material is increased, the velocity may be further reduced.

The imager may generate an image that captures or represents propagation delay through an obstructing material, for example, through image elements corresponding to a scattered field or reflection. By way of illustration, a location of a spot in the generated image, associated with a dominant reflection from the subject's body (e.g., interfacing with or proximate to the material) may indicate or provide a means to infer a propagation delay through a corresponding material. For example, the imager may locate a scattered field associated with an obstructing dielectric material, relative to a position of the subject. The location of the scattered field (e.g., relative to a surface of the subject's body, may indicate a propagation delay due to the obstructing dielectric material.

In a given material, propagation delay may depend on the propagation distance within the material along the path of propagation. For example, the thicker the material or the longer the propagation path, the longer the measured or determined delay. The analyzer may determine from the image at least one of: the delay and a thickness of the first material. The radar system may determine a thickness of the first material from a time delay between a third reflection of the radiation and the first reflection. The third reflection may be from a surface of the first material, e.g., an outward facing surface nearer to the radar system (e.g., the transmitter).

This surface of the first material may be determined by the radar system to be located near to the surface of the body corresponding to the first reflection. For example, the thickness or propagation distance through the material may be determined or estimated by the different in time of receiving/detecting the first and third reflections, or a difference in distance between the corresponding surface of the first material and the surface of the body, relative to a detector of the radar system. The difference in distance may be determined based on the time delay between a third reflection of the radiation and the first reflection. For example, the time delay may represent delay due to a longer propagation path corresponding to twice the estimated thickness of the material.

The imager may generate the image based on reconstruction of reflectivity functions of field scattering objects. The reflectivity function reconstructed when the subject is wearing a dielectric material can be quite different from when the subject is wearing a metallic material. In the case of a metallic material, all the wave energy may be reflected from the front of the material (the side facing the radiation source), while for a dielectric material, part of the wave travels through the material, is reflected on the chest of the subject under test, then travels again through the material and then propagates towards the radar system. This effect of traveling through a dielectric medium can reduce the speed of propagation of the wave when compared with free space propagation. Therefore a reflection that should appear to be in the front of the subject can appear delayed in the image.

In some embodiments, the analyzer, or a user, may determine that a second material residing on or proximate to the surface of the body comprises a metallic material, based on an abrupt variation in pixel intensity in the image. The analyzer may apply a deconvolution process to removes a Point Spread Function (PSF) response from the image, for example, when the image is corrupted by the PSF response resulting from the radar pulse shape and the angular field of view of a corresponding synthetic aperture. A user may be able to detect or recognize the abrupt variation in the processed image. In certain embodiments, the analyzer may employ an algorithm to detect for any abrupt variation in pixel intensity, e.g., a variation exceeding a predefined threshold. In some embodiments, the pixel intensity in the generated image may be proportional to electric currents coinciding with that pixel. If the material placed in the pixel under study is a good conductor (e.g., no energy penetrates in the material under test), reconstruction of the currents by the imager may provide an estimation of the position of the currents in the domain. Thus, a shape of the metallic object may be estimated with an accuracy given by the resolution of the radar system, e.g., in the image. In some embodiments, a variation not exceeding a predefined threshold may be attributed to a non-metallic (e.g., a dielectric) material.

A location of a detected variation may be used to identify if the material is metallic or dielectric. For example, if the variation is external to the body of the subject (e.g., on the side of the receiver), the corresponding material is likely to be not a dielectric. If the variation is located within the subject, this effect may have been caused by the propagation delay through a dielectric material, as described above. A user or the analyzer may determine that the first material comprises a dielectric material based on detection of the delay in propagation (e.g., based on a comparison of the measured reflections).

Referring now to (207), and in some embodiments, the analyzer may determine, based on the delay, at least one of: the first material and a dielectric constant of the first material. The analyzer may determine, from the same image, the thickness of the dielectric material and a delay in reflection due to the dielectric constant. The analyzer may determine the dielectric constant based at least in part on the estimated or measured thickness of the first material. The analyzer may determine a dielectric constant or relative permittivity of the first material, for example, based on (6) as described above. In some embodiments, the system may determine the dielectric constant of the first material from a predefined map between delay characteristics and corresponding dielectric constant values. For example, the map may include a pre-characterized delay per unit thickness value corresponding to a particular dielectric constant value.

The first material may be identified (e.g., by the analyzer, or by referencing against known dielectric constants of materials. In some embodiments, the dielectric constant value, as determined, may be used to identify the dielectric material, alone or in combination with other information (such as a shape or profile of the material, or accompanying metallic or other structures used with the material). The first material may be determined (e.g., by the analyzer, or by referencing against known dielectric constants of materials) to comprise a certain type of explosive material based on the dielectric constant. In some embodiments, the system may identify the first material from a predefined map between delay characteristics and corresponding materials. For example, the map may include a pre-characterized delay per unit thickness value corresponding to a particular dielectric material. The map may include dielectric materials of a certain pertinent category (e.g., an explosive or otherwise potentially dangerous substance) and/or dielectric materials expected within a certain context (e.g., airport travel), so as to exclude an overly broad range of materials having the same or a similar dielectric constant.

In some embodiments, the analyzer or radar system may compensate for the presence of clothing or other material, in determining a dielectric constant or identifying a dielectric material of interest. For example, the analyzer or radar system may account for propagation delay through clothing or other incidental materials, may ignore their effect (e.g., if negligible or below a certain threshold), and/or provide an expected margin of error, e.g., in the calculated dielectric constant value. In certain embodiments, the analyzer or radar system may account for a known or detected gap or distance between a material of interest and the "obstructed" surface of the subject's body. For example, the thickness value (e.g., $d_{obj}$ value as applied to (6)) may be adjusted based on a known gap or distance.

It should be understood that the systems described above may provide multiple ones of any or each of those components and these components may be provided on either a standalone machine or, in some embodiments, on multiple machines in a distributed system. In addition, the systems and methods described above may be provided as one or more computer-readable programs or executable instructions embodied on or in one or more articles of manufacture. The article of manufacture may be a floppy disk, a hard disk, a CD-ROM, a flash memory card, a PROM, a RAM, a ROM, or a magnetic tape. In general, the computer-readable programs may be implemented in any programming language, such as LISP, PERL, C, C++, C#, PROLOG, or in any byte code language such as JAVA. The software programs or executable instructions may be stored on or in one or more articles of manufacture as object code.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

We claim:

1. A method of identifying a material on a body of a person using electromagnetic radiation, comprising:
    a) measuring, by a radar system, a first reflection of radiation incident on a body of a person, the first reflection from a surface of the body;
    b) measuring, by the radar system, a second reflection of the radiation through a material residing on or proximate to the surface of the body;
    c) measuring, by the radar system, a third reflection of the radiation from a surface of the material;
    d) generating, by a processor of the radar system, (i) a first electromagnetic-based image depicting the first reflection in relation to a location of the person, (ii) a second electromagnetic-based image depicting the second reflection in relation to the location of the person and (iii) a third electromagnetic-based image depicting the third reflection in relation to the location of the person, wherein the depiction of the second reflection is displaced relative to the depiction of the first reflection by a first displacement on the image corresponding to a delay in the second reflection due to propagation of a portion of the radiation through the material, and the depiction of the third reflection is displaced relative to the depiction of the first reflection by a second displacement on the image; and e) determining, by the processor, using a ratio of the first displacement and the second displacement, a dielectric constant of the material.

2. The method of claim 1, comprising determining that the material comprises a dielectric material based on detection of the delay.

3. The method of claim 1, comprising determining, by the radar system, a thickness of the material from a time delay between the third reflection of the radiation and the first reflection.

4. The method of claim 1, comprising generating the electromagnetic-based imaging using high resolution phase based (HR-PB) processing using a free space wavenumber.

5. The method of claim 1, comprising determining that the material comprises a first type of explosive material based on the dielectric constant.

6. The method of claim 1, comprising determining the dielectric constant of the material from a predefined map between delay characteristics and corresponding dielectric constant values.

7. The method of claim 1, comprising identifying the material from a predefined map between delay characteristics and corresponding materials.

8. The method of claim 1, comprising determining the dielectric constant of the material by summing the ratio with a value of 1, and taking a square of the sum.

9. The method of claim 1, wherein the material is a first material, and further comprising determining that a second material residing on or proximate to the surface of the body comprises a metallic material, based on a variation in pixel intensity in the image that exceeds a predefined threshold.

10. The method of claim 1, comprising determining, from the image, at least one of: the delay and a thickness of the material.

11. A system of identifying a material on a body of a person using electromagnetic radiation, comprising:

an electromagnetic-based imager providing a measurement of a first reflection of radiation incident on a body of a person, the first reflection from a surface of the body, a measurement of a second reflection of the radiation through a material residing on or proximate to the surface of the body, and a third reflection of the radiation from a surface of the material; and an analyzer generating (i) a first electromagnetic-based image depicting the first reflection in relation to a location of the person, (ii) a second electromagnetic-based image depicting the second reflection in relation to a location of the person and (iii) a third electromagnetic-based image depicting the third reflection in relation to a location of the person, wherein the second reflection is displaced relative to the first reflection by a first displacement on the image corresponding to a delay in the second reflection due to propagation of a portion of the radiation through the material, and the third reflection is displaced relative to the first reflection by a second displacement on the image, and determining, by the processor using a ratio of the first displacement and the second displacement, a dielectric constant of the material.

12. The system of claim 11, wherein the analyzer determines that the material comprises a dielectric material based on detection of the delay.

13. The system of claim 11, wherein the analyzer determines a thickness of the material from a time delay between the third reflection of the radiation and the first reflection.

14. The system of claim 13, wherein the analyzer generates the electromagnetic-based imaging using high resolution phase based (HR-PB) processing using a free space wavenumber.

15. The system of claim 11, wherein the analyzer determines that the material comprises a first type of explosive material based on the dielectric constant.

16. The system of claim 11, wherein the analyzer determines the dielectric constant of the material from a predefined map between delay characteristics and corresponding dielectric constant values.

17. The system of claim 11, wherein the analyzer identifies the material from a predefined map between delay characteristics and corresponding materials.

18. The system of claim 11, wherein the analyzer determines the dielectric constant of the material by summing the ratio with a value of 1, and taking a square of the sum.

19. The system of claim 11, wherein the material is a first material, and wherein the analyzer determines that a second material residing on or proximate to the surface of the body comprises a metallic material, based on a variation in pixel intensity in the image that exceeds a predefined threshold.

20. The system of claim 11, wherein the analyzer determines, from the image, at least one of: the delay and a thickness of the material.

* * * * *